US009453764B2

(12) United States Patent
Hofmeister et al.

(10) Patent No.: US 9,453,764 B2
(45) Date of Patent: Sep. 27, 2016

(54) DEVICES AND METHODS FOR ANALYZING LAYERS OF SAMPLES

(71) Applicant: H2Optx Inc., San Jose, CA (US)

(72) Inventors: Rudolf J. Hofmeister, San Jose, CA (US); Donald A. Ice, Milpitas, CA (US); Scott W. Tandy, Los Altos Hills, CA (US)

(73) Assignee: H2Optx Inc., San Jose, CA (US)

( * ) Notice: Subject to any disclaimer, the term of this patent is extended or adjusted under 35 U.S.C. 154(b) by 0 days.

(21) Appl. No.: 14/805,221

(22) Filed: Jul. 21, 2015

(65) Prior Publication Data

US 2016/0216199 A1 Jul. 28, 2016

Related U.S. Application Data

(60) Provisional application No. 62/108,003, filed on Jan. 26, 2015.

(51) Int. Cl.
| | |
|---|---|
| *G01N 21/25* | (2006.01) |
| *G01J 3/42* | (2006.01) |
| *G01J 3/44* | (2006.01) |
| *G01J 3/06* | (2006.01) |
| *G01J 3/10* | (2006.01) |
| *B01D 46/00* | (2006.01) |
| *B01D 46/42* | (2006.01) |
| *G01N 1/06* | (2006.01) |

(Continued)

(52) U.S. Cl.
CPC ............. *G01J 3/42* (2013.01); *B01D 46/0002* (2013.01); *B01D 46/42* (2013.01); *G01J 3/00* (2013.01); *G01J 3/06* (2013.01); *G01J 3/10* (2013.01); *G01J 3/44* (2013.01); *G01N 1/06* (2013.01); *G01N 21/01* (2013.01); *G01N 21/25* (2013.01); *G01N 21/253* (2013.01); *G01N 21/33* (2013.01); *G01N 21/3504* (2013.01); *G01N 21/3577* (2013.01); *G01N 21/65* (2013.01); *G01N 23/00* (2013.01); *G01N 33/15* (2013.01); *G01N 35/10* (2013.01); *G01N 2021/0106* (2013.01)

(58) Field of Classification Search
CPC ........ G01N 21/25; G01N 33/15; G01N 1/06; B01D 46/00; B01D 46/42
USPC .............................................. 356/300, 72–73
See application file for complete search history.

(56) References Cited

U.S. PATENT DOCUMENTS

| 7,213,413 B2 | 5/2007 | Battiste et al. |
| 2005/0264813 A1 | 12/2005 | Giakos |

(Continued)

FOREIGN PATENT DOCUMENTS

WO 2004/031749 A2 4/2004

*Primary Examiner* — Abdullahi Nur
(74) *Attorney, Agent, or Firm* — Maschoff Brennan

(57) ABSTRACT

The present disclosure generally relates to systems, devices and methods for analyzing and processing samples or analytes. In one example configuration, a method of analyzing an analyte includes shaving a first layer of a plurality of layers of an analyte to expose a first surface of an analyte. The method includes positioning the first surface of the analyte over a window of a hyperspectral analyzation subassembly. The method further includes scanning the first surface of the analyte by the hyperspectral analyzation subassembly to obtain information regarding the analyte proximate the first surface. Other systems, devices and methods are disclosed herein.

23 Claims, 26 Drawing Sheets

(51) Int. Cl.

| | |
|---|---|
| *G01N 33/15* | (2006.01) |
| *G01N 21/01* | (2006.01) |
| *G01N 23/00* | (2006.01) |
| *G01N 35/10* | (2006.01) |
| *G01N 21/3504* | (2014.01) |
| *G01J 3/00* | (2006.01) |
| *G01N 21/33* | (2006.01) |
| *G01N 21/3577* | (2014.01) |
| *G01N 21/65* | (2006.01) |

(56) References Cited

U.S. PATENT DOCUMENTS

| | | |
|---|---|---|
| 2006/0002594 A1 | 1/2006 | Clarke et al. |
| 2009/0002702 A1 | 1/2009 | Maier et al. |
| 2009/0010388 A1 | 1/2009 | Stahly et al. |
| 2012/0302892 A1 | 11/2012 | Lue et al. |
| 2015/0330902 A1* | 11/2015 | Mourey ............... G01N 21/658 356/301 |

* cited by examiner

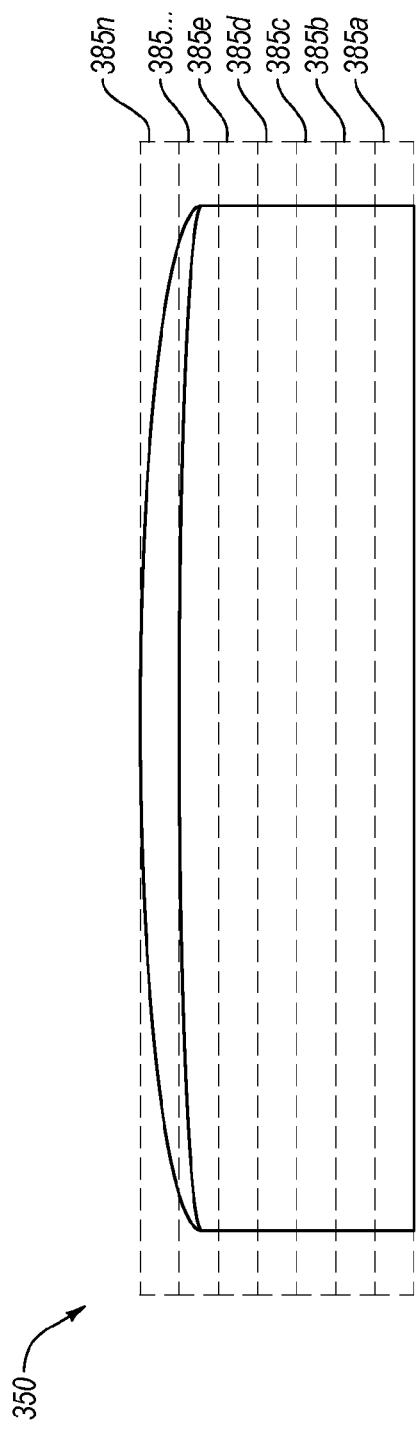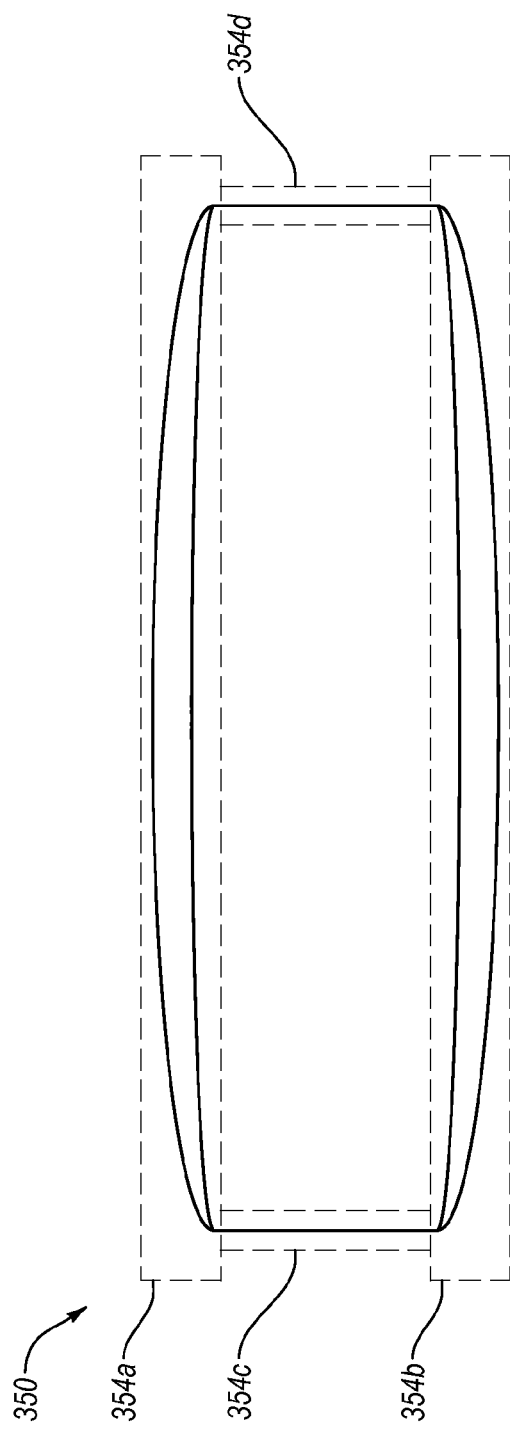

DEVICES AND METHODS FOR ANALYZING LAYERS OF SAMPLES

CROSS-REFERENCE TO RELATED APPLICATIONS

This application claims priority to U.S. patent application Ser. No. 62/108,003, filed Jan. 26, 2015, entitled "SYSTEMS, DEVICES AND METHODS FOR ANALYZING AND PROCESSING SAMPLES," which is incorporated by reference in its entirety.

BACKGROUND

The present disclosure generally relates to systems, devices and methods for analyzing and processing samples. Information about the samples may be obtained through a variety of analysis techniques such as microscopy, spectroscopy, spectrometry, chromatography, as well as many others. Information about the samples may be used to conduct experiments; improve, control, or monitor production processes; or improve, control, or monitor manufactured products.

The claimed subject matter is not limited to embodiments that solve any disadvantages or that operate only in environments such as those described above. This background is only provided to illustrate examples of where the present disclosure may be utilized.

SUMMARY

The present disclosure generally relates to systems, devices and methods for analyzing and processing samples or analytes. Information about the samples may be obtained through a variety of analysis techniques such as microscopy, spectroscopy, spectrometry, chromatography, as well as many others. Information about the samples may be used to conduct experiments; improve, control or monitor production processes; or improve, control or monitor manufactured products.

In an example configuration, a method of analyzing an analyte includes shaving a first layer of a plurality of layers of an analyte to expose a first surface of an analyte. The method includes positioning the first surface of the analyte over a window of a hyperspectral analyzation subassembly. The method further includes scanning the first surface of the analyte by the hyperspectral analyzation subassembly to obtain information regarding the analyte proximate the first surface.

In an example embodiment, a system for analyzing layers of an analyte includes a paring subassembly with at least one paring member sized and shaped to remove layers of the analyte to expose underlying surfaces of the analyte. The system includes a mandrel subassembly including a mandrel to retain the analyte as the layers of the analyte are removed. The system includes an actuation subassembly to actuate the mandrel or the paring member in one or more directions of movement with respect to one another as the analyte is positioned against the paring member to remove at least a portion of a first layer of the analyte.

In another example embodiment, a system for analyzing layers of an analyte includes a paring subassembly with at least one paring member sized and shaped to remove layers of an analyte to expose underlying surfaces of the analyte. The system includes a mandrel subassembly including a mandrel defining a receptacle sized and shaped to retain the analyte as the layers of the analyte are removed. The system includes an actuation subassembly to: actuate the mandrel or the at least one paring member in one or more directions of movement with respect to one another to displace the analyte across the at least one paring member to remove a first layer of the analyte to expose a first surface; and actuate the mandrel to position the exposed first surface of the analyte over a window of a hyperspectral analyzation subassembly to be scanned by the hyperspectral analyzation subassembly through the window.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

BRIEF DESCRIPTION OF THE DRAWINGS

FIGS. 8A-8E are views of the analyte that may be analyzed by the device of FIG. 7A.

DETAILED DESCRIPTION

Figure 1:
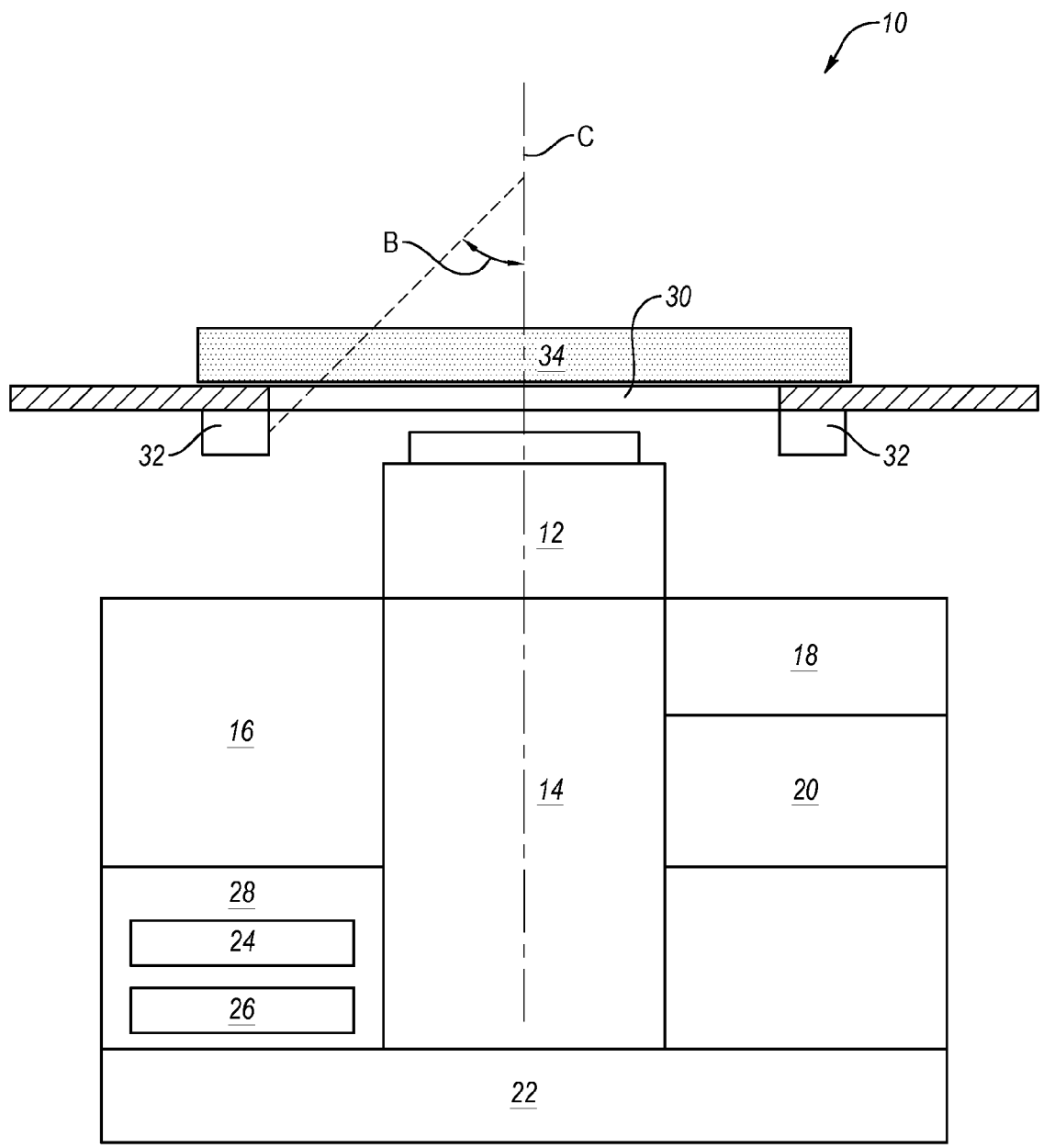
FIG. 1 is a schematic diagram of a non-limiting embodiment of a system configured to analyze or process samples.

Reference will be made to the drawings and specific language will be used to describe various aspects of the disclosure. Using the drawings and description in this manner should not be construed as limiting the scope of the disclosure. Additional aspects may be apparent in light of the disclosure, including the claims, or may be learned by practice. The drawings are non-limiting, diagrammatic, and schematic representations of example embodiments, and are not necessarily drawn to scale.

The terms and words used in the following description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

The term "granular sample" may include single crystalline particles, polycrystalline particles, granulated particles, granulated multicomponent particles, micronized particles, single component or blended substances, or any combination thereof. In some aspects, "granular sample" may include any powdered sample.

The term "analyte" may refer to a substance whose physical and/or chemical constituents are to be analyzed, identified and/or measured.

The terms "assembly" or "subassembly" may be used interchangeably to refer to any portion of a device or system as may be indicated by context, and may refer to different portions of a device or system when used in different contexts.

The term "vacuum" may refer to a pressure differential in a system or a portion of a system. The term "vacuum" may include a positive or negative pressure differential. In some aspects, the term "vacuum" may refer to systems or portions of systems with an internal pressure less than or greater than atmospheric pressure.

The present disclosure generally relates to systems, devices and methods for analyzing and processing samples. The disclosed systems may include modular aspects that permit the systems to be configured to analyze or process different types of samples, which may referred to as analytes. Additionally or alternatively, the systems may include modular aspects to permit the systems to be configured to analyze or process samples by one or more different methods or techniques. Information about the samples may be obtained through a variety of analysis techniques such as microscopy, spectroscopy, spectrometry, chromatography, as well as many others. Information about the samples may be used to conduct experiments; improve, control, or monitor production processes; or improve, control, or monitor manufactured products.

In some configurations, the disclosed systems may be used in a lab setting to conduct experiments. For example, the configuration of the systems may be selected for powders, liquids, gases, emulsions, suspensions, solids, homogeneous combinations, heterogeneous combinations, pills, tablets, materials, biological samples, and/or any suitable combinations thereof.

In other configurations, the disclosed systems may be used as a part of production line to analyze and process samples to obtain information about aspects of the production line, such as characteristics of finished products and/or of intermediaries of the products. The disclosed systems may be implemented as in-process monitoring systems integrated into a production line and configured to analyze one or more properties of a sample as it is being produced.

FIG. 1 is a schematic diagram of an example embodiment of a system 10 that may be configured to analyze or process samples. The system 10 may include an objective 12 optically coupled to an optical multiplexer 14. The optical multiplexer 14 may be optically coupled to a sensor 16, an emitter 18 and/or a detector 20. A sample 34 may be positioned on and/or over a window 30 that is optically coupled to the objective 12 and/or the optical multiplexer 14. The system 10 may include a platform 22 that may be configured to move portions of the system 10 relative to the sample 34. In some configurations, the platform 22 may be configured to move portions of the system 10 in three directions of movement (linear, non-linear, angular, etc.). At least some portions of the system 10 can be translated in any of the three directions relative to the sample 34. In operation, the movement of the platform 22 may contribute to focusing optical components of the system 10, scanning the sample 34, engaging or disengaging portions of the system 10, and/or a combination thereof.

The emitter 18 may be configured to emit radiation to analyze the sample 34. The emitter may emit any suitable electromagnetic radiation to analyze and/or process the sample 34. For example, the emitter 18 may emit visible light, ultraviolet light, X-rays, infrared or any other suitable radiation. In some configurations, the emitter 18 may be a laser or diode. In some configurations, the emitter 18 may be a Raman laser source.

The detector 20 may be configured to detect radiation from the sample 34. For example, the detector 20 may be configured to detect radiation from the sample 34 resulting from the radiation from the emitter 18 incidenting the sample 34. The detected radiation may permit information regarding the sample 34 to be obtained. In some configurations, the detector 20 may be a Raman spectrometer.

An emitter 32 may be positioned around the window 30 and/or proximate the sample 34 and configured to emit radiation that may incident the sample 34. In some configurations, the emitter 32 may be a ring encircling the window 30. In other configurations, the emitter 32 may be one or more discrete emitter elements positioned at various suitable positions with respect to the window 30 and/or the sample 34. In some configurations, the emitter 32 may be an electromagnetic radiation source or an electromagnetic radiation ring.

In some configurations, the system 10 may include a controller 28 configured to control the operation of at least a portion of the system 10. The controller 28 may include a processor 24 that executes instructions stored in memory 26. The processor 24 and memory 26 can be incorporated into the system 10, as illustrated. In other configurations, the processor 24 and/or the memory 26 can be located in a controller 28 external to the system 10. For example, the system 10 may be controlled and/or operated by a computer system coupled to the system 10.

The memory 26 can include executable instructions that control the operation of the system 10. For example, the memory 26 can comprise instructions that when executed by the processor 24 causes the emitter 32 to expose the sample 34 to emitted radiation (e.g., electromagnetic, visible light, ultraviolet, heat, microwave, or other radiation). Depending on the properties of the sample 34 and the characteristics of the emitted radiation, some of the radiation projected on the sample 34 may pass through the sample 34, some may be absorbed by the sample 34, and/or some may be reflected by the sample 34.

Emissions from the irradiated sample 34 (for example, by reflection or fluorescence), may travel through the objective 12 into the optical multiplexer 14. At least a part of the emissions from the sample 34 may be directed to the sensor 16 by the optical multiplexer 14. The sensor 16 may detect characteristics of the received radiation, such as energy level, wavelength, or other characteristics. The characteristics of the received radiation may be used to determine characteristics of the sample 34. For example, in some configurations, the characteristics of the received radiation may be used to determine aspects of the sample 34.

The system 10 may be configured to use the sensor 16 to obtain information about the sample 34. For example, the sensor 16 may be an image sensor (e.g., a color camera, or monochromatic camera) configured to obtain images of the irradiated sample 34. The controller 28 may be configured to receive, process, modulate, and/or convert signals from the sensor 16 to obtain information about the sample 34. In some configurations, the controller 28 may be configured to generate images of the sample 34 from the signals from the sensor 16. The controller 28 can employ image analyzing algorithms to: (i) compare particle luminance magnitude of the sample 34; (ii) detect particle sizes of the sample 34; (iii) compare particle sizes against other sizes in the sample 34 or to a database of particle sizes; (iv) compare particle sizes against other shapes in the sample 34 or to databases of particle shapes, and/or any suitable combinations of these algorithms or others.

In some configurations, the emitter 32 emits electromagnetic radiation at a given wavelength of a plurality of wavelengths into the sample 34. The emitter 32 may include, for example, one or more emitters capable of producing electromagnetic radiation within a terahertz range. In another example, a wavelength of the electromagnetic radiation may be within a range of approximately 0.01 to 10 nanometers. This range comprises X-ray wavelengths. In yet another example, the electromagnetic radiation produced by the emitter 32 may be varied in wavelength from blue to ultraviolet light. In another example, the emitter 32 emits white light. The responsiveness of the sample 34 is determined by the controller 28 by examining color of the one or more of the components of the sample 34.

The emitter 32 may be multiple sources that each provides a unique narrow band wavelength of electromagnetic radiation. For example, each of the emitters 32 may output any of red, blue, and green light. The emitters 32 may include light emitting diodes and/or lasers.

In yet other configuration, the emitter 32 may expose the mixture sample to near infrared or mid infrared light. The emitters 32 may produce broad band radiation or successive bursts of narrow bands of radiation. In one example, the emitters 32 may selectively expose the mixture sample to many different wavelengths of electromagnetic radiation and analyzing how each wavelength affects components of the sample 34. This example configuration may be used to analyze samples of unknown composition, although other configurations are contemplated.

The objective 12 may include a high, low, or variable magnification objective lens. The objective 12 may include a high magnification lens that permits viewing of small particles (e.g., less than 20 microns in size) and/or viewing small features on larger particles. The objective 12 may include low magnification lenses used to provide a large field of view, which may permit rapid identification of regions of interest in an image. The magnification of the objective 12 may be selectively varied by the controller 28 to locate particles at low power settings. The controller 28 may be configured execute analytical processes to identify the particle by shape and/or size. The controller 28 may be configured to zoom in where particles of certain characteristics are identified.

In some configurations, an optical filter may be optically coupled prior to the sensor 16 to block frequencies of radiation that may damage the sensor 16 and/or provide undesired effects on the information obtained by the sensor 16. In some configurations, the optical filter may be selected depending on the wavelength of the electromagnetic radiation that is output by the emitter 32. In some configurations, the optical filter may be configured to block light at wavelengths of approximately 425 nanometers to 700 nanometers. In other configurations, higher wavelength filters may be used in combination with lower wavelength filters. For example, higher wavelength filters may be used, for example, with Raman lasers, while lower wavelength filters may be used with, for example, ultraviolet light. In some configurations, the emitter 32 may be a laser optically coupled with a long pass filter. In another example, the emitter 32 may be a light emitting diode (LED) optically coupled to a long pass filter.

The system 10 may include one or more optical filters used to block the excitation wavelength for the sensor 16 to permit the sensor 16 to obtain usable images. The controller 28 may be configured to activate the emitter 32 for a set period of time, such as ten seconds. Images may be captured of the sample 34 by the sensor 16 to determine the responsiveness of at least portions of the sample 34 by detecting timing and decay of response of the one or more of the components of the sample 34 to the radiation.

The system 10 may use additional measurement algorithms to detect and differentiate components of the sample 34 from one another using particle size and shape. For example, the controller 28 of the system 40 can use various image processing methods to determine an aspect ratio for particles of components of the sample 34. Also, the controller 28 of the system 10 can calculate size, shape, fuzziness, angularity, brightness, and combinations thereof for components of the sample 34.

The size and/or shape of components of the sample 34 may be used to detect the presence of paper fibers or other contaminates. For example, if a particle is detected, its size and shape may be calculated using image processing. The size and shape may be compared to a database of particle sizes and corresponding shapes. If no reasonable comparison is found, a particle may be determined to be a contaminate. Contaminates may be catalogued and/or stored in a database. In some configurations of the system 10, contaminants may be isolated, concentrated, separated, stored, and/or disposed, as will be described in further detail below with respect to FIGS. 9A-9D. The algorithm used by the controller 28 may be selected based on the composition of the sample 34, if an expected composition for the sample 34 is known.

With continued reference to FIG. 1, the emitter 32 may emit electromagnetic radiation into the mixture sample at an angle B that is specified with reference to a central axis C of the window 30. In such configurations, radiation may enter the sample 34 at the angle B.

The controller 28 may be configured to detect, track and/or count a number of excited particles in the sample 34. The controller 28 may be further configured to calculate a concentration of a selected component of the sample 34. For example, when the controller 28 has located a number of a first component of the sample 34, the controller 28 may calculate a volume of the first component of the sample 34, for example, using image analysis. The overall area of the particles of the first component relative to the total area of the image may be used to estimate the volume by weight of the first component, if the size of the first component particles is known.

In some configurations, Raman spectroscopy may be used to verify and/or analyze the presence, size, and/or shape of components of the sample 34. In such configurations, the emitter 18 may be a Raman laser source and the detector 20 may be a Raman spectrometer. The emitter 18 may be controlled, for example, by the controller 28 to expose the sample 34 to a wavelength of laser light. The laser light may be focused onto a small portion of the sample 34 where candidate particles are fluorescing (e.g., responsive). Images may be transferred by the optical multiplexer 14 to the Raman spectrometer detector 20 via a Raman spectrometer interface. The Raman spectrometer 20 and or the Raman spectrometer interface may be integrated into the system 10 or may be a standalone external feature. In some circumstances, the identification of the candidate particles may be confirmed using Raman spectroscopy.

In other configurations, the emitter 18 may instead be an X-ray source, near infrared source, infrared source, ultra violet source, and/or any source of radiation suitable for an intended application. The system 10 may include any suitable combinations or permutations of these or other radiation sources, depending on the type of analytes being analyzed and/or the desired information to be obtained.

In some configurations, the system 10 may be used to obtain three-dimensional models of the sample 34. A three dimensional model may be a composition of many images obtained using permutations of positions in three axes X, Y, and Z. For example, the objective 12 may be moved in three directions of movement along three axes X, Y, and Z by the platform 22. The Z-axis may be aligned with the central axis C of the window 30. Depending on the width of the field of view of the sensor 16, the objective 12 may be moved sequentially along the window 30 in the X and Y direction. At each X and Y location, the platform 22 may translate the objective 12 from an initial position along the Z-axis towards the window 30, in increments (e.g., one micron increments, etc.). At each increment, the sensor 16 may obtain an image of the illuminated sample 34. The system 10 may be capable of obtaining images at any given depth into the sample 34. These images may each be associated with their respective X, Y, and Z location information. The images may be assembled together by the system 10, for example via the controller 28, to form a three-dimensional model of the sample 34.

The three-dimensional imaging of the sample 34 may be used to calculate responsive particles of a component of the sample 34 on a surface of the sample 34, as well as particles located within the sample 34 at a specified distance inside the surface of the sample 34.

A method of analyzing the sample 34 using the system 10 will be described in further detail. The method may include capturing high resolution color images of the sample 34 exposed with multiple color lighting (e.g., a range of wavelengths of electromagnetic radiation). The multiple color lighting of the sample 34 may occur at multiple angles of incidence and/or from different directions. For example, the angle B may be selectively varied during illumination of the sample 34. The method may include processing the images to identify possible particles of a first component of the sample 34 by size, color, and/or shape. The method may include using Raman scanning and analysis to positively identify candidate particles as particles of the first component. This may be accomplished using a Raman signature for particles of the first component as a baseline. The method may include calculating a particle area to percentage-by-weight calculation where a percentage-by-weight is correlated to a percentage-by-area of particles of the first component observed in the images. The method may be repeated until a statistically significant particle area is located in one or more components of the sample 34 and/or multiple samples.

The system 10 may include any suitable aspects described in U.S. patent application Ser. No. 14/507,637, entitled "OPTICAL AND CHEMICAL ANALYTICAL SYSTEMS AND METHODS" and U.S. patent application Ser. No. 14/454,483, entitled "ANALYSIS AND PURGING OF MATERIALS IN MANUFACTURING PROCESSES," which are both incorporated herein by reference in their entirety and for all purposes. The concepts described with respect to the system 10 may be implemented in a variety of configurations and may be combined with other aspects of this disclosure, as may be indicated by context.

Turning to FIGS. 2A-2E, an example embodiment of a system 40 that can be configured to analyze or process samples will be described. In some configurations, the system 40 may be an implementation of the system 10 of FIG. 1. Accordingly, the system 40 may include any suitable aspects described with respect to system 10, as may be indicated by context.

Figure 2A:
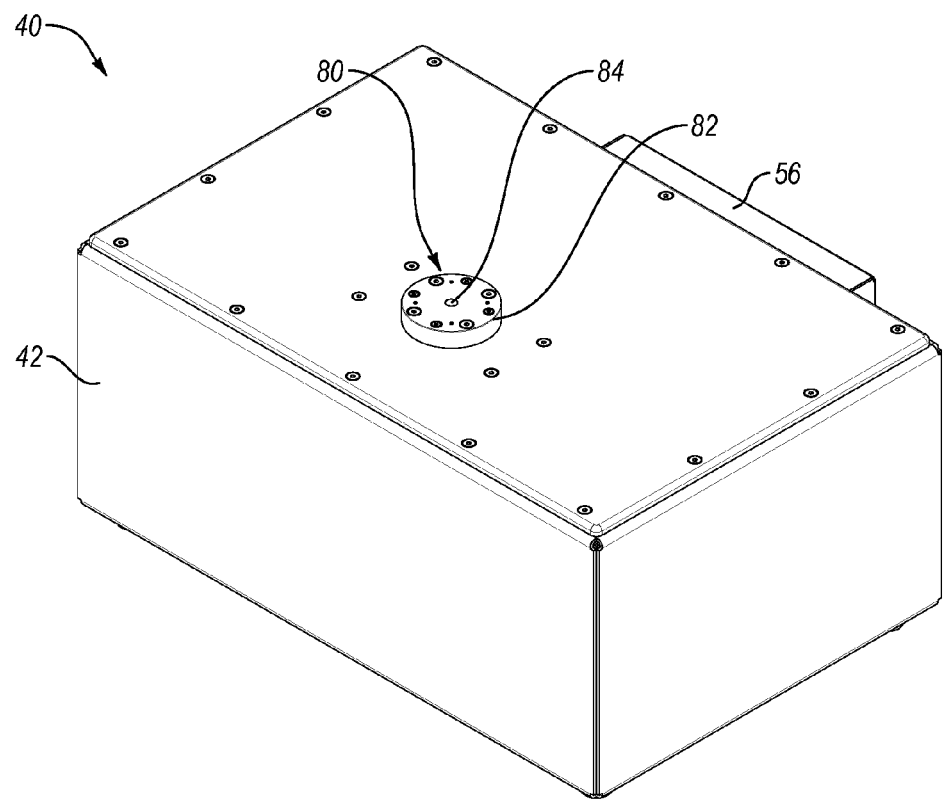
FIGS. 2A-2B are perspective views of a non-limiting embodiment of a system configured to analyze or process samples.
Figure 2B:
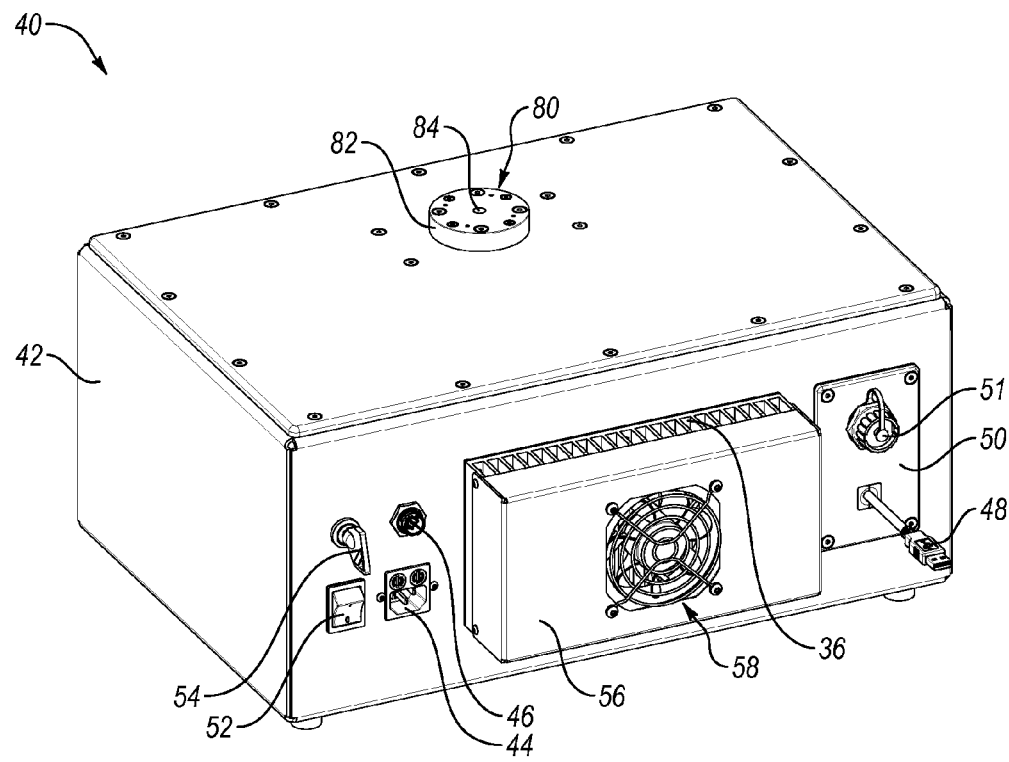

FIGS. 2A and 2B are perspective views of a portion of the system 40. As illustrated, the system 40 may include a housing 42 surrounding at least a portion of the system 40. The system 40 may include an interface assembly 80 configured to interface with other portions of the system 40, as will be described in further detail below. The interface assembly 80 may include a body 82 and a window 84 that is configured to permit light to travel through at least a portion of the interface assembly 80. The window 84 may be at least partially transparent or translucent and/or may be configured to convey, direct, collimate and/or focus light travelling through the interface assembly 80. In the illustrated configuration, the interface assembly 80 is positioned on a top portion of the housing 42, although other suitable configurations are contemplated.

Turning to FIG. 2B, the system 40 may include a first connector 44, a second connector 46, and a third connector 48 connecting portions of the system 40 inside of the housing 42 to portions of the system 40 exterior to the housing 42. The connectors 44, 46, and 48 may be electronic connectors configured to transmit data, power and/or control signals. The system 40 may include a switch 52 that may be configured to activate and/or turn on at least portions of the system 40.

As illustrated, the first connector 44 may be a socket configured to receive a first plug to electrically couple the system 40 and the second connector 46 may be a socket configured to receive a second plug to electrically couple the system 40. The first connector 44 may permit the system 40 to be electrically coupled to a power source, for example, an alternating current (AC) power supply. The second connector 46 may be a socket configured to transmit data, power and/or control signals in and/or out of portions of the system 40 inside of the housing 42.

As illustrated, the third connector 48 may be a cable connector coupled with the housing 42 by a connector panel 50. In the illustrated configuration, the third connector 48 is a Universal Serial Bus (USB) cable extending from the system 40. In such configurations, the third connector 48 may transmit one or more of data, power and/or control signals. In other configurations, the third connector 48 may be any suitable connector that may or may not correspond to an interface standard or interface protocol (such as USB, firewire, etc.). The connector panel 50 may include a connector 51 which may be, for example, a fluid connector or a vacuum connector.

In some configurations, the third connector 48 may permit the system 40 to be coupled to electronic components such as computers, computer systems, computer interfaces, user interfaces, mobile devices and/or any other suitable electronic component. In such configurations, the electronic component may provide power and/or control signals to the system 40 via the third connector 48. Additionally or alternatively, the electronic component may receive data signals and/or feedback from the system 40 via the third connector 48. In other configurations, the third connector 48 may permit the system 40 to be coupled to other components of the system 40. In such configurations, portions of the system 40 (for example, portions inside of the housing 42) may provide power and/or control signals to at least one other component of the system 40 via the third connector 48. Additionally or alternatively, portions of the system 40 (for example, portions inside of the housing 42) may receive data signals and/or feedback from at least one other component of the system 40 via the third connector 48. The connector panel 50 may be removably coupled to the housing 42 to permit connectors of different types to be coupled to the system 40.

In some configurations, the system 40 may include non-illustrated connectors such as a fluid connector configured to permit fluid (gaseous, liquid, or otherwise) to travel into or out of the housing 42. Fluid connectors may permit the system 40 to be coupled with, for example, vacuum lines, pressurized gas lines, cooling fluid lines, water lines, liquid lines, or other suitable fluids. Although the illustrated configuration includes three connectors 44, 46, and 48, the system 40 may include any suitable amount of connectors and may include connectors of any suitable type. The configurations of the connectors may be selected based on the desired configuration and/or functionality of the system 40, as applicable. Additionally or alternatively, the configuration of the connectors may be selected depending on modular components that may be coupled, added and/or activated with the system 40.

The system 40 may include a security assembly 54 that may be configured to lock the system 40 from being operated. For example, the security assembly 54 may disable portions of the system 40 such as emitters from operating to facilitate in preventing inadvertent exposure to electromagnetic radiation. In some configurations, the security assembly 54 may disconnect power from one or more emitters of the system 40. The security assembly 54 may facilitate in preventing operation of the system 40 in a potentially unsafe manner and/or may facilitate in preventing inadvertent exposure to electromagnetic radiation when the system 40 is being serviced. In the illustrated configuration, the security assembly 54 is a key and a lock configured to receive the key. In other configurations, the security assembly 54 may include any suitable electronic and/or mechanical locking mechanism. For example, biometric and/or cryptographic key locking mechanisms (password, passphrase, personal identification number, etc.) may be employed. The security assembly 54 may facilitate safe operation of the system 40 by permitting only qualified users to operate the system 40.

The system 40 may include a temperature management assembly 56 configured to facilitate temperature control of at least a portion of the system 40. For example, the temperature management assembly 56 may heat or cool portions of the system 40, such as those positioned within the housing 42, to maintain desired or suitable operating conditions. As illustrated for example in FIG. 2E, in some configurations the temperature management assembly 56 may include a heat sink 36 positioned between a first ventilator 38 and a second ventilator 58. The heat sink 36 may be configured to transmit heat by conduction and maintain separation between the interior and the exterior of the housing 42. The first ventilator 38 and second ventilator 58 may be configured to drive air and/or other fluids along the surfaces of the heat sink 36 to facilitate heat management. In other configurations, the temperature management assembly 56 may include any suitable heating and/or cooling mechanisms.

Although in the illustrated configuration components of the system 40 such as the switch 52, the security assembly 54, the temperature management assembly 56, and the connectors 44, 46, 48 are positioned on one end of the housing 42, such components may be positioned at any suitable position in the system 40. In some configurations, at least one of the components may be positioned, for example, inside of the housing.

Figure 2C:
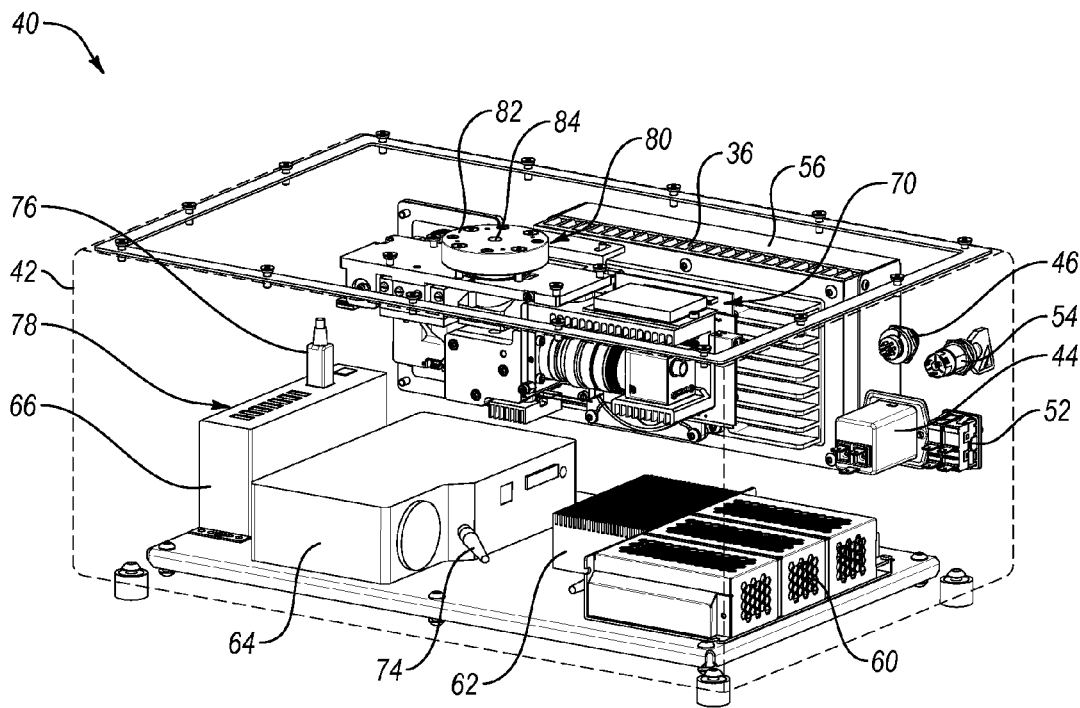
FIGS. 2C-2E are perspective views of a portion of the system of FIG. 2A.
Figure 2D:
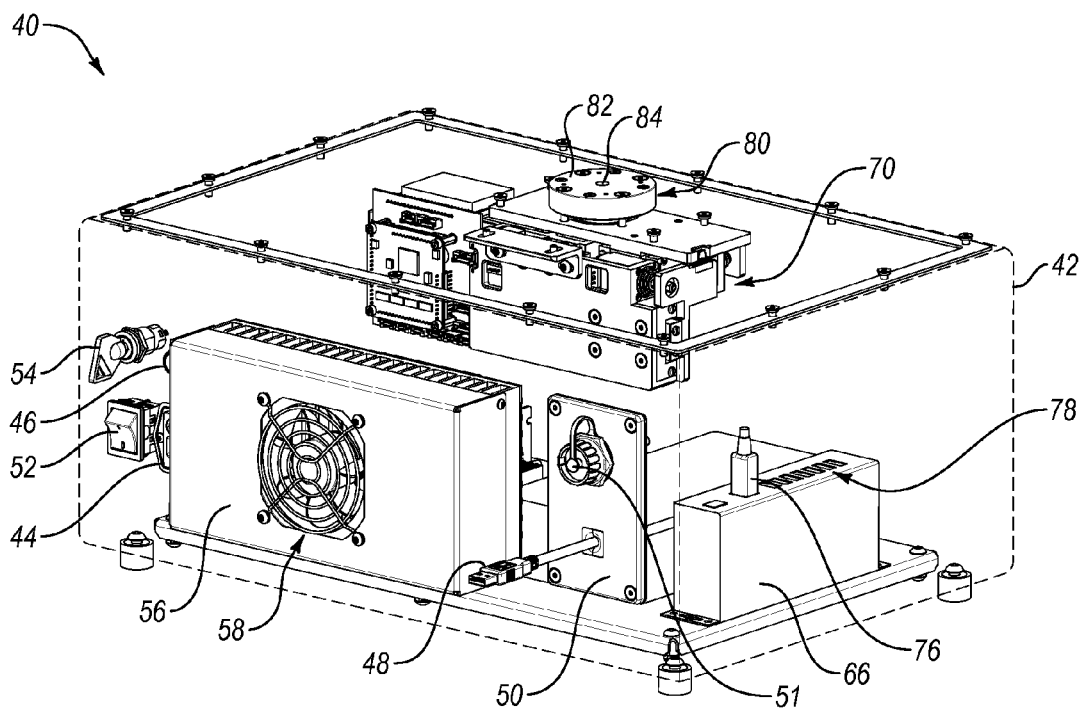
Figure 2E:
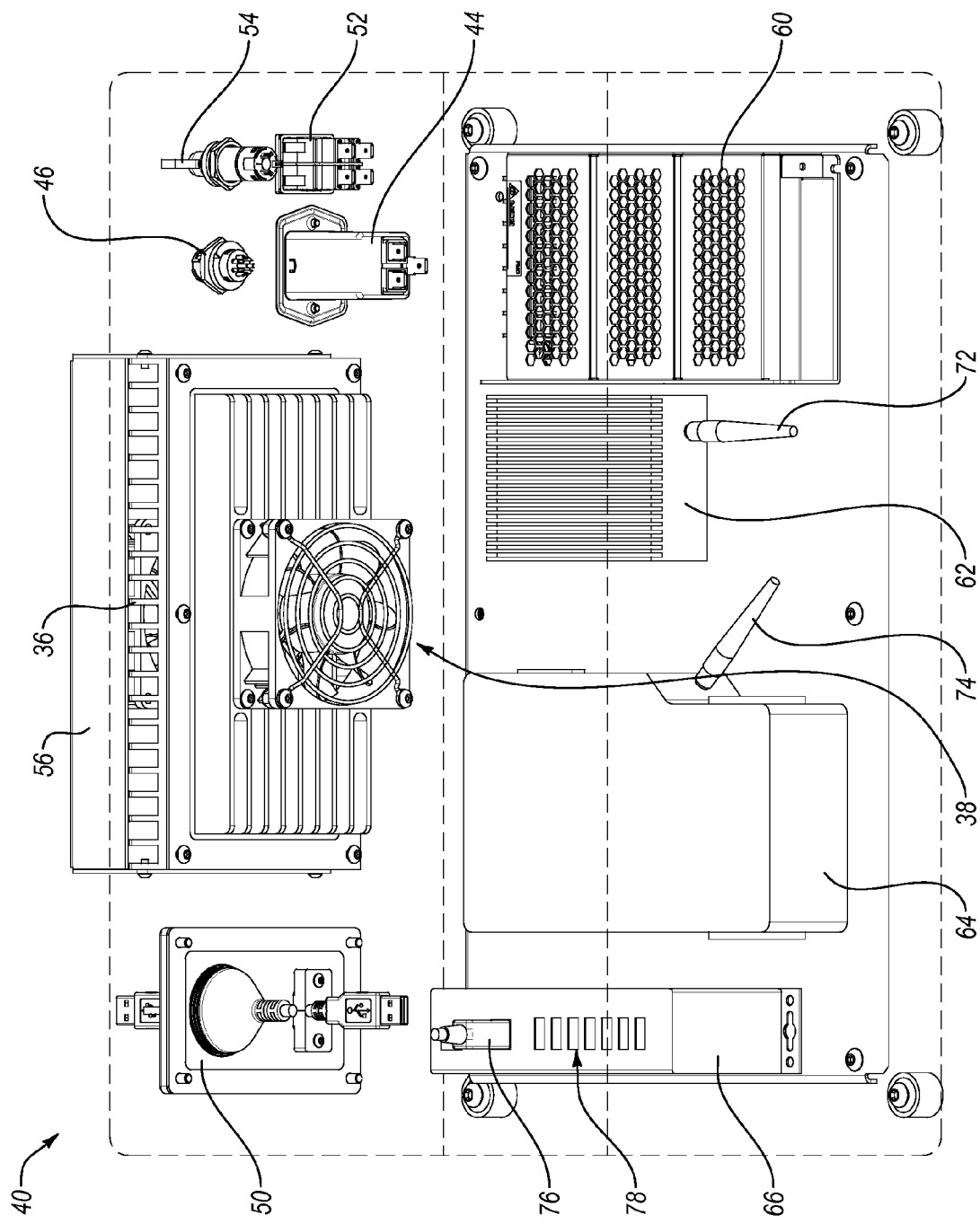

FIGS. 2C, 2D, and 2E illustrate portions of the system 40 inside of the housing 42, which is represented by dashed lines. As illustrated, the system 40 may include a head assembly 70, a power assembly 60, an emitter assembly 62, a detector assembly 64, and an electronic assembly 66 positioned inside of the housing 42. The head assembly 70 may be mechanically coupled to the interface assembly 80 and/or optically coupled to receive and/or transmit electromagnetic radiation to/from the interface assembly 80. The head assembly 70 is omitted from FIG. 2E to illustrate other portions of the system 40.

The power assembly 60 may be configured to control, distribute and/or modulate power supplied to portions of the system 40. In some configurations, the power assembly 60 may be electrically coupled with various portions of the system 40 by electrical couplings such as cables (not illustrated).

The emitter assembly 62 may include an emitter such as the emitter 18 and the detector assembly 64 may include a detector such as detector 20 as described with respect to FIG. 1. The emitter assembly 62 may include a first interface 72 and the detector assembly 64 may include a second interface 74. In some configurations, the first and second interfaces 72, 74 may be optical interfaces configured to optically couple the emitter assembly 62 and/or the detector assembly 64. For example, the first interface 72 may optically couple the emitter assembly 62 to the head assembly 70 via, for example, an optical cable (not illustrated). In another example, the second interface 74 may optically couple the detector assembly 64 to the head assembly 70 via, for example, an optical cable (not illustrated). The emitter assembly 62 may be configured to transmit radiation to the head assembly 70 and/or the detector assembly 64 may be configured to receive radiation from the head assembly 70 to obtain information about samples. In some configurations, the emitter assembly 62 may be a Raman laser source assembly and the detector 20 may be a Raman spectrometer assembly.

In an example implementation, the head assembly 70 may include an objective, an optical multiplexer, a sensor and/or platform such as the objective 12, the optical multiplexer 14, the sensor 16, and/or platform 22 as described with respect to FIG. 1. Additionally or alternatively, the head assembly 70 may include a controller such as controller 28 as described with respect to FIG. 1. The head assembly 70 will be described in further detail below with respect to FIGS. 3A-3F.

The electronic assembly 66 may be configured to distribute data, power and/or control signals to various portions of the system 40. The electronic assembly 66 may include one or more connectors 76, 78 configured to couple various components of the system 40. In some configurations, the electronic assembly 66 may be a USB hub.

Figure 3A:
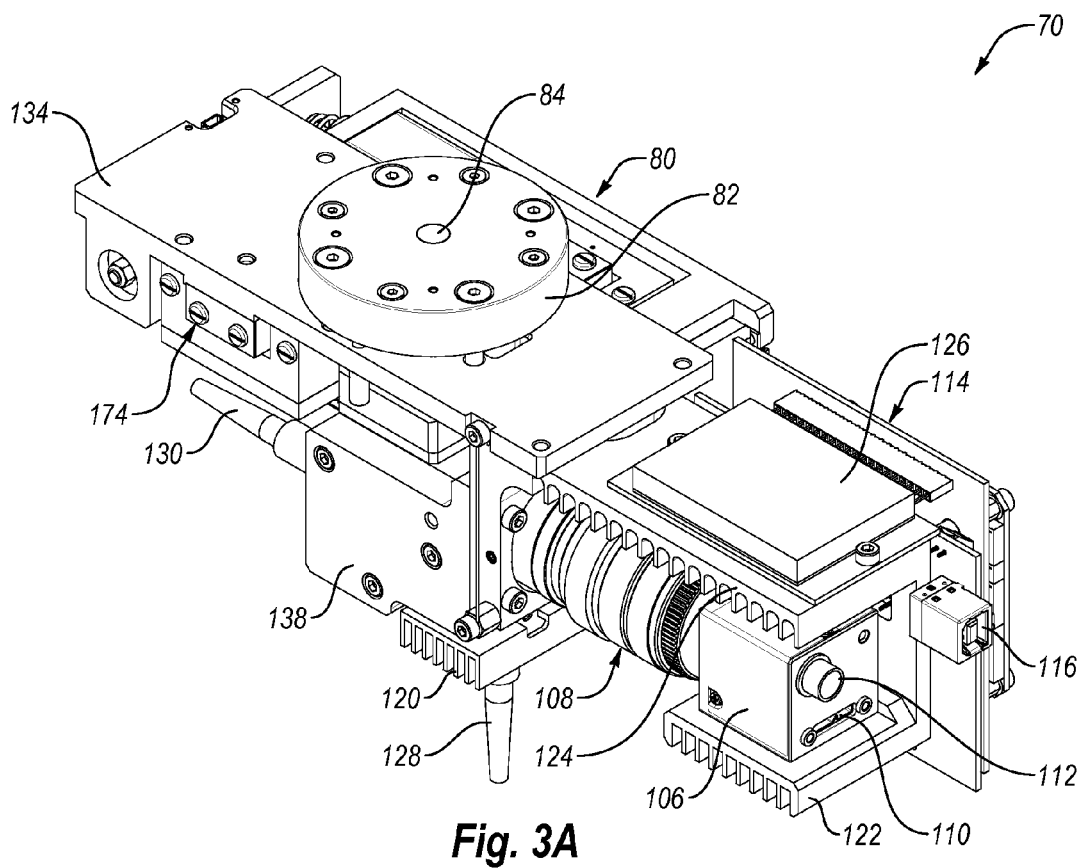
FIGS. 3A-3D are perspective views of a head assembly of the system of FIGS. 2A-2B.
Figure 3B:
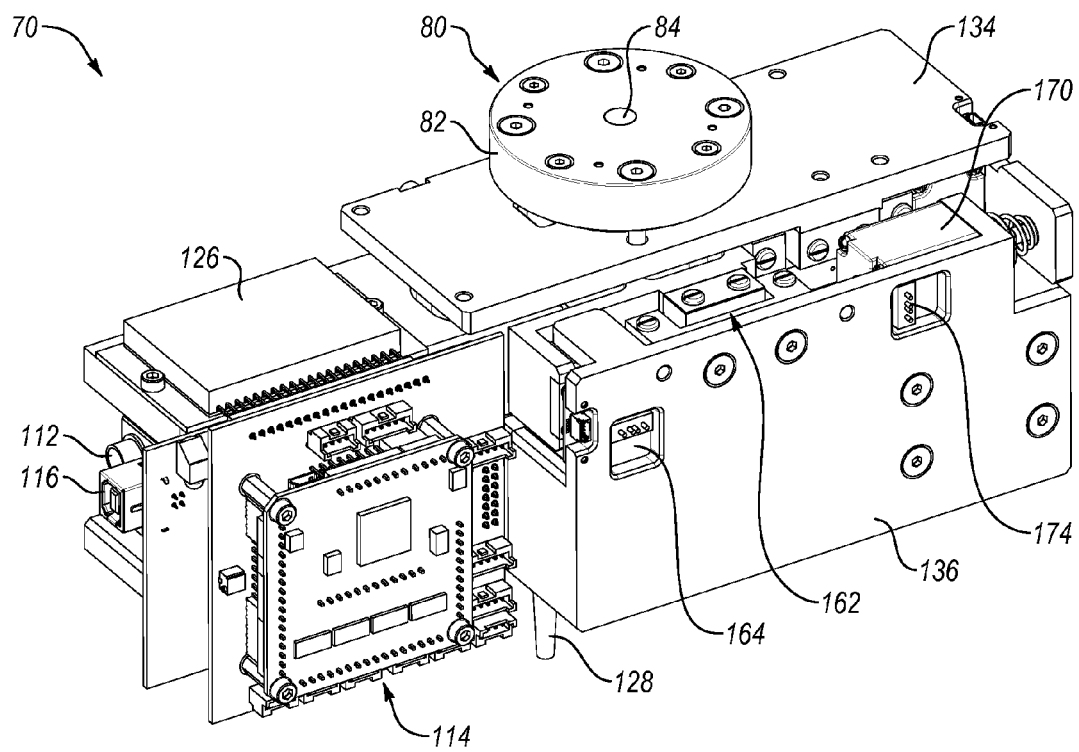
Figure 3C:
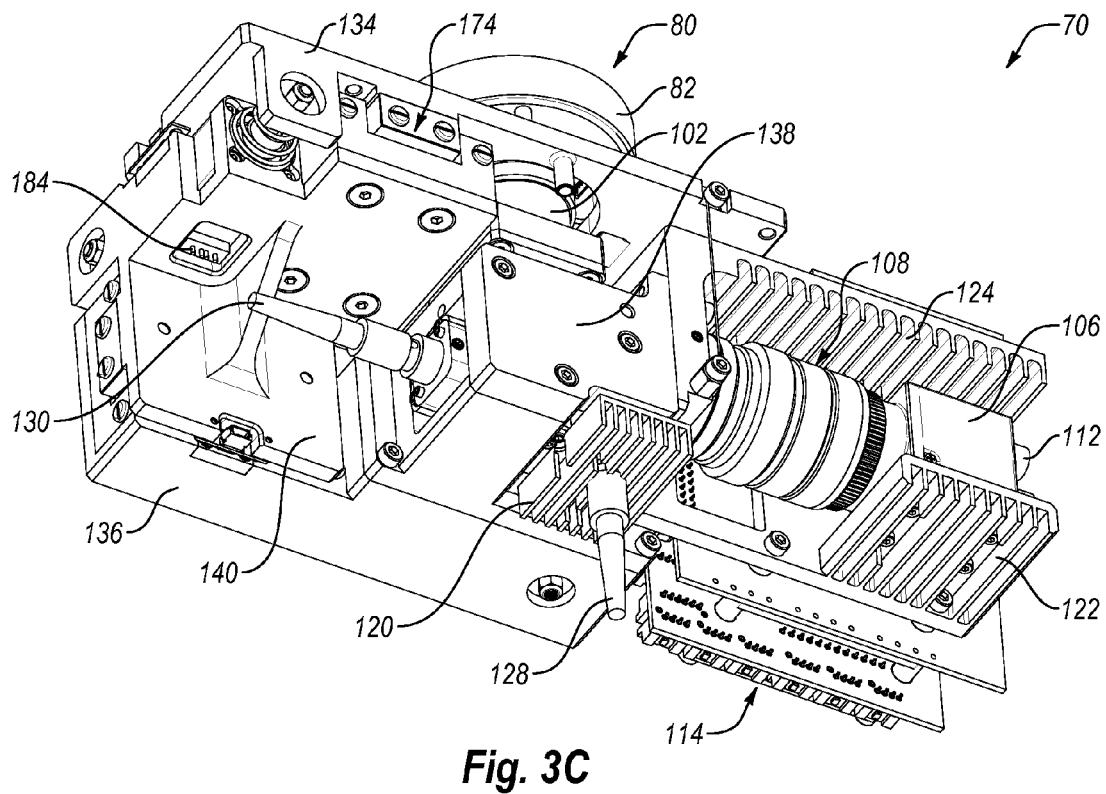
Figure 3D:
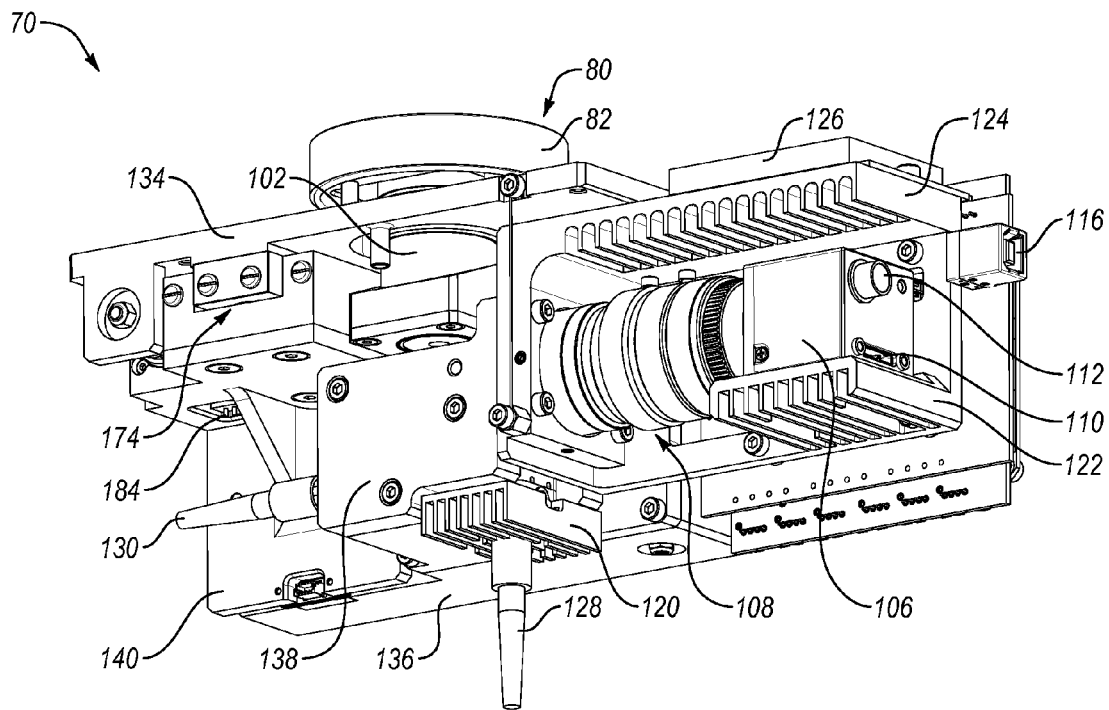
Figure 3E:
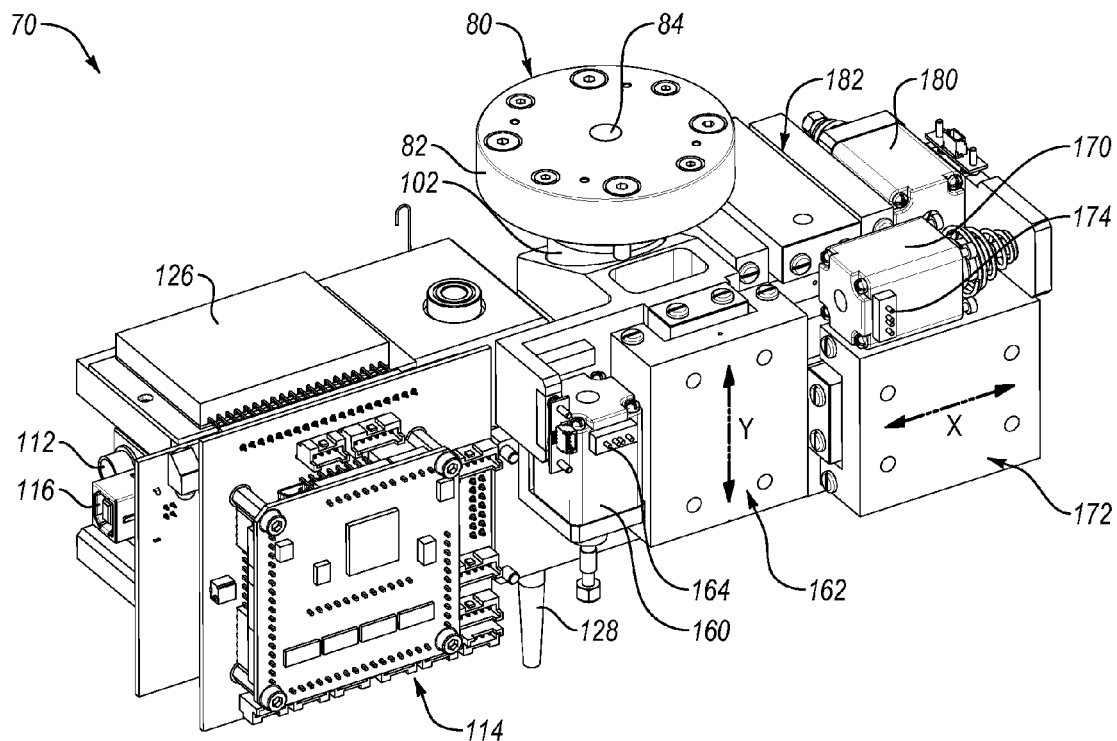
FIGS. 3E-3F are perspective views of a portion of the head assembly of FIGS. 3A-3D.
Figure 3F:
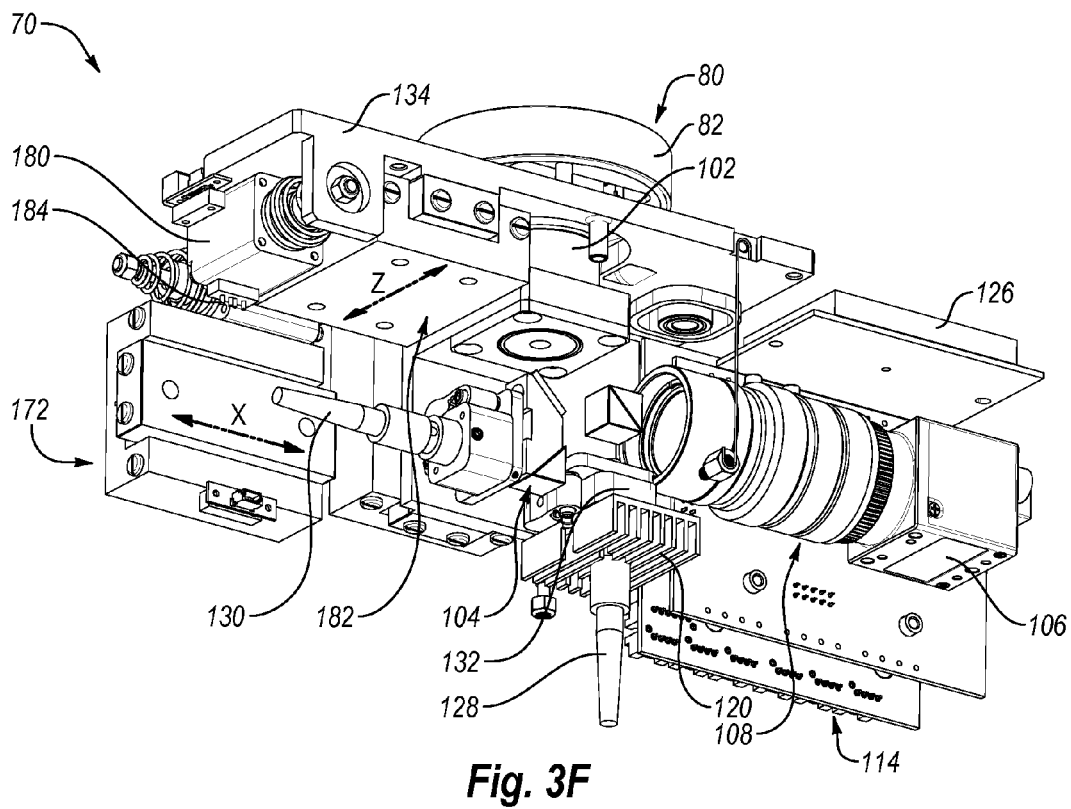

FIGS. 3A-3D illustrate perspective views of an example implementation of the head assembly, denoted generally at 70. FIGS. 3E and 3F illustrate the head assembly 70 with some portions omitted to illustrate other details of the head assembly 70. As illustrated, the head assembly 70 may be optically coupled to receive and/or transmit electromagnetic radiation to/from the interface assembly 80. Specifically, the head assembly 70 may include an objective 102 (see for example FIGS. 3E and 3F) coupled to the interface assembly 80. The objective 102 may include optics configured to convey, direct, collimate and/or focus electromagnetic radiation travelling between the head assembly 70 and the interface assembly 80. As illustrated for example in FIG. 3F, the objective 102 may be optically coupled to an optical multiplexer 104. The optical multiplexer 104 may be configured to distribute electromagnetic radiation travelling through the head assembly 70 and/or other portions of the system 40. Additionally or alternatively, the optical multiplexer 104 may be configured to convey, direct, collimate and/or focus electromagnetic radiation travelling through the head assembly 70 and/or other portions of the system 40.

The head assembly 70 may include a sensor 106 configured to detect characteristics of received electromagnetic radiation such as energy level, wavelength, or other characteristics (for example, as described above with respect to the system 10). The characteristics of the received radiation may be used to determine characteristics of samples. In some configurations, the sensor 106 may be an image sensor (e.g., a color camera, or monochromatic camera) configured to obtain images of samples. An optical assembly 108 may be optically coupled between the optical multiplexer 104 and the sensor 106. The optical assembly 108 may be configured to convey, direct, collimate and/or focus electromagnetic radiation travelling between the optical multiplexer 104 and the sensor 106. The sensor 106 may include a first connector 110 and/or a second connector 112 configured to transmit data, power and/or control signals between the sensor 106 and other portions of the head assembly 70.

The head assembly 70 may be configured such that portions of the head assembly 70 may be moved with respect to the interface assembly 80. For example, in some configurations, the head assembly 70 may move at least the objective 102 with respect to the interface assembly 80. In some configurations, the head assembly 70 may be configured to move portions of the head assembly 70 in three directions of movement (linear, non-linear, angular, etc.), for example, along three axes: X, Y, and Z. In operation, the movement of portions of the head assembly 70 such as the objective 102 may contribute to focusing and/or scanning the samples.

As illustrated for example in FIG. 3E, the head assembly 70 may include one or more motors or actuators 160, 170, 180. Each of the actuators 160, 170, 180 may be coupled to a corresponding slide 162, 172, 172 configured to the permit portions of the head assembly 70 (e.g., the objective 102) to move with respect to the interface assembly 80. In the illustrated configuration, each actuator 160, 170, 180 and slide 162, 172, 172 corresponds to a direction of movement X, Y, and Z. In non-illustrated configurations, the head assembly 70 may include less or more directions of movement, and/or such directions may or may not be orthogonal to one another. Each of the actuators 160, 170, 180 may include a corresponding connector 164, 174, and 184. The connectors 164, 174, 184 may be configured to couple the actuators 160, 170, 180 to other portions of the head assembly 70. The connectors 164, 174, 184 may be electronic connectors configured to transmit data, power and/or control signals. The connectors 164, 174, 184 may transmit power and/or control signals to drive and/or operate the actuators 160, 170, 180 to move portions of the head assembly 70 with respect to the interface assembly 80. The head assembly 70 may include stops corresponding with each of the directions of movement to limit the movement of the portions of the head assembly 70 with respect to the interface assembly 80.

In the illustrated configuration, portions of the head assembly 70 actuate in three linear directions of movement. In other configurations, the head assembly 70 may actuate in any suitable directions of movement, and such directions of movement may not be linear (e.g., rotational, angular, non-linear, etc.). In some configurations, the head assembly 70 may include mirrors that may be rotated and/or actuated to deflect optical beams rather than moving other portions of the head assembly 70.

The head assembly 70 may include an electronic assembly 114 with a controller configured to control the operation of at least a portion of the system 10. The electronic assembly 114 may be configured to distribute power and/or control signals to other components of the head assembly 70. The electronic assembly 114 may be configured to receive data signals from other components of the head assembly 70, such as the sensor 106.

Specifically, the electronic assembly 114 may include one or more connectors 116 configured to couple the electronic assembly 114 to other portions of the head assembly 70. The connector 116 may be electronic connector configured to transmit data, power and/or control signals. The connector 116 may be coupled to other portions of the head assembly 70, such as the sensor 106, the actuators 160, 170, 180 and/or other components. Additionally or alternatively, the connector 116 may be coupled to other portions of the system 40.

The electronic assembly 114 may include a processor that executes instructions stored in memory. As illustrated, the electronic assembly 114 may be incorporated into the head assembly 70. In other configurations, the electronic assembly 114 may be a separate component external to the head assembly 70. For example, the head assembly 70 may be controlled and/or operated by a computer system coupled to the head assembly 70. The electronic assembly 114 can include executable instructions that control the operation of the head assembly 70. For example, the electronic assembly 114 can include instructions that when executed cause the head assembly 70 to analyze and/or scan one or more samples.

The head assembly 70 may include an electronic assembly 126, which in some configurations may be a temperature management assembly configured to manage the temperature of portions of the head assembly 70. For example, the electronic assembly 126 may be configured to cool portions of the head assembly 70. The electronic assembly 126 may include a Peltier device, Peltier heat pump, solid state refrigerator, and/or a thermoelectric cooler. The electronic assembly 126 may include a controller configured to manage the temperature of portions of the head assembly 70 by controlling the operation of a Peltier device, Peltier heat pump, solid state refrigerator, and/or a thermoelectric cooler.

As illustrated for example in FIG. 3F, the head assembly 70 may include an emitter 132 configured to emit radiation to analyze samples. The emitter 132 may emit any suitable electromagnetic radiation to analyze and/or process samples. For example, the emitter 132 may emit visible light, ultraviolet light, X-rays, infrared or any other suitable radiation. In some configurations, the emitter 132 may be a laser or diode. In some configurations, the emitter 132 may be a Raman laser source. The emitter 132 may be optically coupled with the optical multiplexer 104. In such configurations, the optical multiplexer 104 may be configured to convey, direct, collimate and/or focus electromagnetic radiation from the emitter 132. For example, the optical multiplexer 104 may be configured to direct radiation from the emitter 132 to a sample.

In addition to or as an alternative to the emitter 132, the head assembly 70 may include an optical interface 128 configured to optically couple the head assembly 70 to other components of the system 40. For example, the optical interface 128 may couple the head assembly 70 to an emitter, such as the emitter assembly 62 as described above with respect to FIGS. 2C and 2E. The optical interface 128 may optically couple the head assembly 70 to the emitter assembly 62 via, for example, an optical cable (not illustrated). The emitter assembly 62 may be configured to transmit electromagnetic radiation to the head assembly 70. In such configurations, the optical multiplexer 104 may be configured to convey, direct, collimate and/or focus electromagnetic radiation from the emitter assembly 62. For example, the optical multiplexer 104 may be configured to direct radiation from the emitter assembly 62 to a sample.

The head assembly 70 may include a second optical interface 130 configured to optically couple the head assembly 70 to other components of the system 40. For example, the optical interface 130 may couple the head assembly 70 to a detector, such as the detector assembly 64 as illustrated and described with respect to FIGS. 2C and 2E, for example. The optical interface 130 may optically couple the head assembly 70 to the detector assembly 64 via, for example, an optical cable (not illustrated). The detector assembly 64 may be configured to receive radiation from the head assembly 70 to obtain information about samples. In such configurations, the optical multiplexer 104 may be configured to convey, direct, collimate and/or focus electromagnetic radiation to the detector assembly 64. For example, the optical multiplexer 104 may be configured to distribute radiation from samples to the detector assembly 64.

The head assembly 70 may include one or more support members 134, 136, 138, 140 configured to support, enclose, and/or couple portions of the head assembly 70 to one another. The configuration of the support members 134, 136, 138, 140 may permit portions of the head assembly 70 to move in the X, Y, and Z directions. Additionally or alternatively, the configuration of the support members 134, 136, 138, 140 may limit the range of motion of portions of the head assembly 70 in the X, Y, and Z directions.

The head assembly 70 may include one or more heat sinks 120, 122, 124 configured to facilitate cooling of portions of the head assembly 70. In some configurations, the heat sinks 120, 122, 124 may be configured to cool specific components of the head assembly 70. For example, in the illustrated configuration, the heat sink 120 is configured to cool the emitter 132, the heat sink 122 is configured to cool the sensor 106 and the heat sink 124 is configured to cool the electronic assembly 126 or other portions of the head assembly 70. In other configurations, the head assembly 70 may include more or less heat sinks; the heat sinks 120, 122, 124 may be configured in other manners; or may be omitted entirely. Additionally or alternatively, the temperature of the components of the head assembly 70 may be managed by other temperature control systems and/or mechanisms.

In some configurations, the head assembly 70 may include any suitable aspects as described with respect to the system 10 of FIG. 1.

Figure 4A:
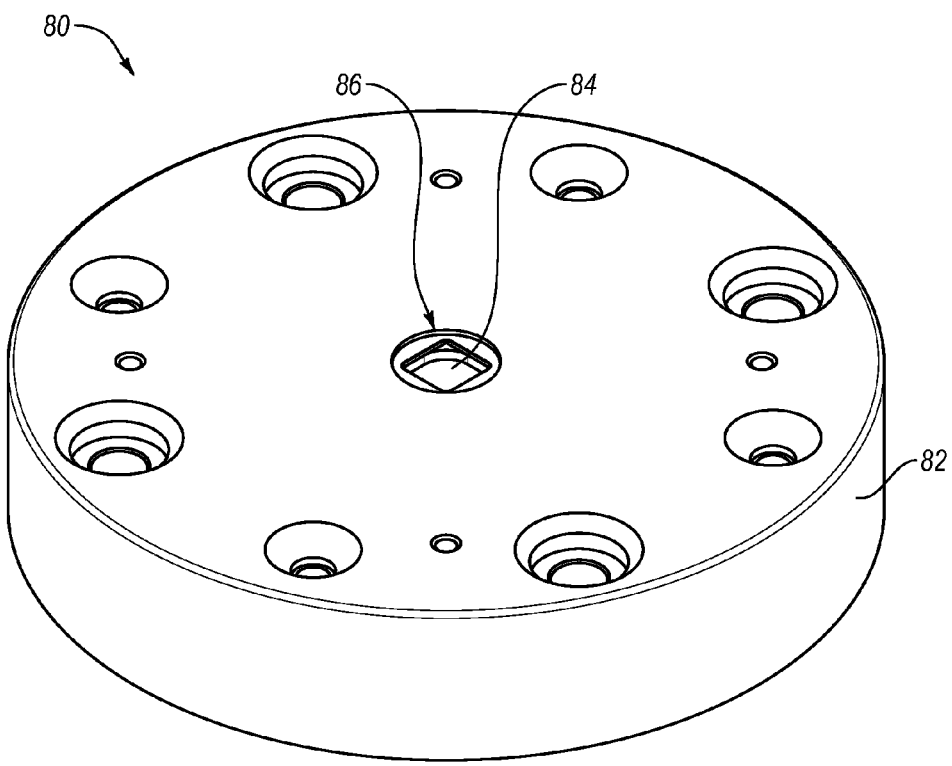
FIGS. 4A-4B are perspective views of an interface assembly of the system of FIGS. 2A-2B.
Figure 4B:
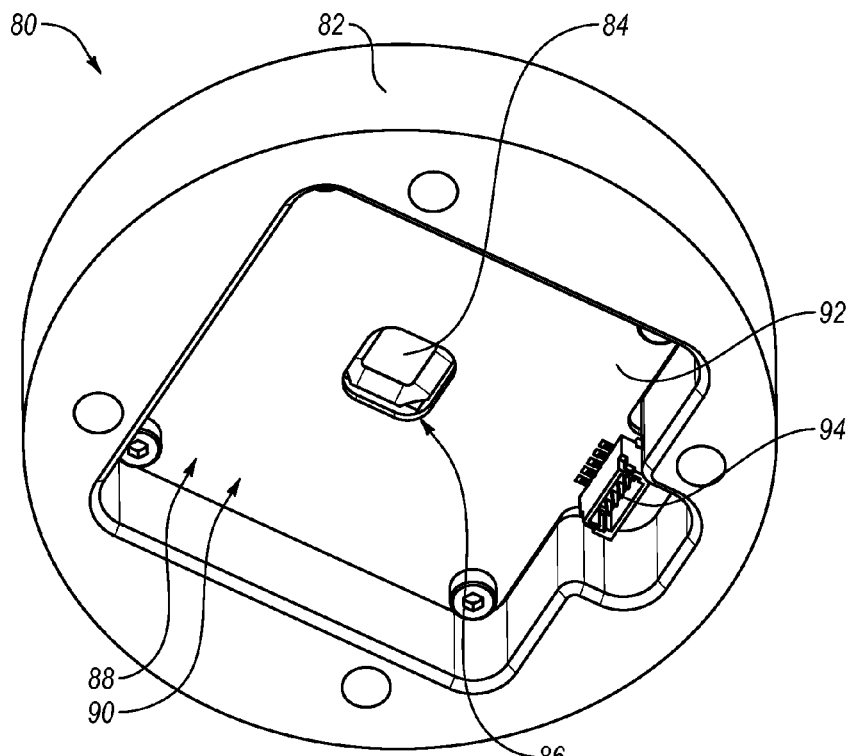

FIGS. 4A and 4B illustrate one example embodiment of the interface assembly, denoted generally at 80, in further detail. The interface assembly 80 may be configured to interface with other portions of the system 40, such as the head assembly 70 and/or other components of the system 40 that will be described in further detail below. As illustrated, the body 82 of the interface assembly 80 defines an aperture 86 extending at least partially through the interface assembly 80. The aperture 86 may be configured (e.g. shaped and/or dimensioned) to permit electromagnetic radiation to travel through at least a portion of the interface assembly 80 to the window 84. The window 84 may be at least partially transparent or translucent and/or may be configured to convey, direct, collimate and/or focus light travelling through the interface assembly 80.

As illustrated for example in FIG. 4B, the body 82 of the interface assembly 80 may define a receptacle 88 with an optoelectronic assembly 90 positioned therein. The optoelectronic assembly 90 will be described in further detail below with respect to FIGS. 5A-5B. The optoelectronic assembly 90 may be removably or non-removably fastened to the body 82 of the interface assembly 80 inside of the receptacle 88. The optoelectronic assembly 90 may include a body 92 and a connector 94 coupled to the body 92. In some configurations, the body 92 may be an electronic board such as a printed circuit board (PCB). The connector 94 may be configured to couple the optoelectronic assembly 90 to other portions of the system 40. The body 92 may include an opening further defining the aperture 86 of the interface assembly 80.

Figure 5A:
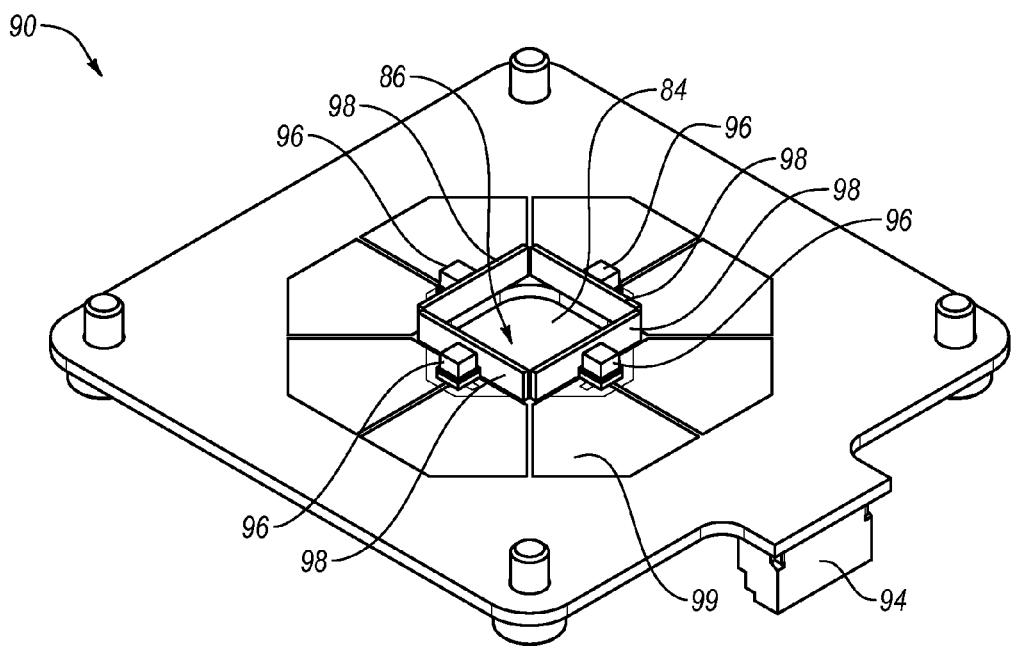
FIGS. 5A-5B are perspective views of a portion of the interface assembly of FIGS. 4A-4B.
Figure 5B:
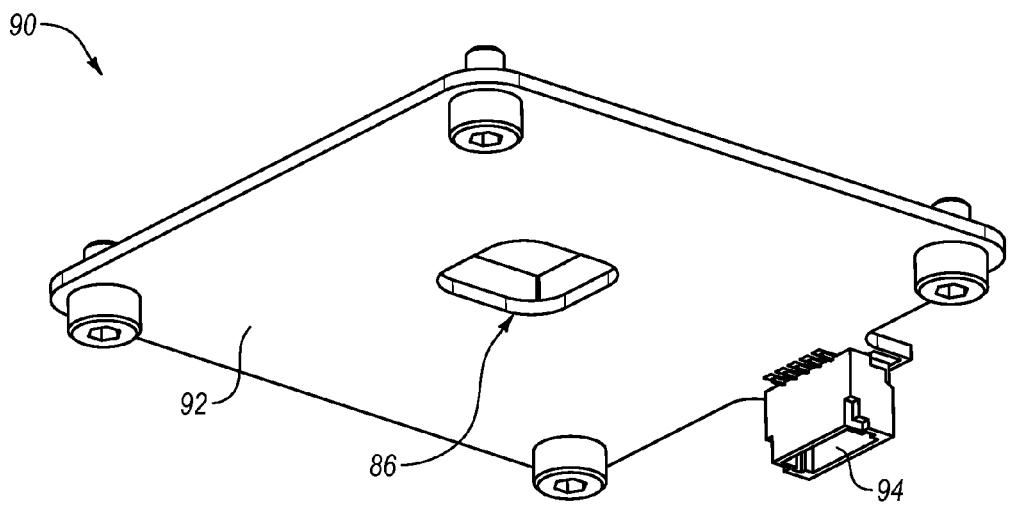

Turning to FIGS. 5A and 5B, the optoelectronic assembly 90 will be described in further detail. As illustrated, the optoelectronic assembly 90 may include one or more emitters 96 positioned around the aperture 86. One or more polarizers 98 may be positioned between each of the emitter 96 and the aperture 86. The emitters 96 may be configured to emit visible light, ultraviolet light, X-rays, infrared or any other suitable radiation. The emitter 96 may be any suitable electromagnetic radiation source. In some configurations, the emitter 96 may be a laser or a diode. In some configurations, the optoelectronic assembly 90 may include multiple emitters 96 and one or more of the emitters 96 may be configured to output electromagnetic radiation of different characteristics from one another. The emitters 96 may be electrically coupled to the connector 94 by any suitable electrical coupling. For example, the emitters 96 may be electrically coupled to the connector 94 by conductive traces printed on the body 92 or running through the body 92. The connector 94 may be coupled to other portions of the system 40. The connector 94 may permit power and/or control signals to be transmitted to the emitters 96. The connector 94 may also permit feedback and/or data to be transmitted from the optoelectronic assembly 90 to other portions of the system 40.

As illustrated for example in FIG. 5A, a heat conductive material 99 may be coupled to the body 92. The heat conductive material 99 may be configured to facilitate managing the temperature of the optoelectronic assembly 90 and/or the interface assembly 80. For example, the heat conductive material 99 may permit heat to be dissipated from portions of the optoelectronic assembly 90 and/or the interface assembly 80. Specifically, heat generated during operation of the emitters 96 may be conducted through the heat conductive material 99 and may dissipate away from the emitters 96. Additionally or alternatively, the heat conductive material 99 may dissipate heat from the polarizers 98 and/or other portions of the interface assembly 80. In some configurations, the heat conductive material 99 may be copper or may at least partially include copper.

Figure 5C:
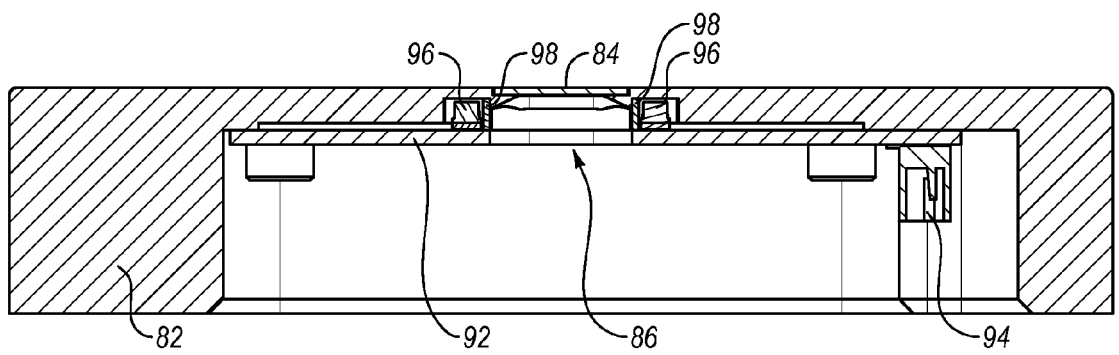
FIG. 5C is a cross-sectional view of the interface assembly of FIGS. 4A-4B.

FIG. 5C illustrates a cross-sectional view of the interface assembly 80 with the optoelectronic assembly 90. In operation, a sample may be positioned over the window 84 and the head assembly 70 may be activated to analyze and/or process the sample. In some configurations, the window 84 may be sealed to the body 82 such that substances may not travel between the window 84 and the body 82 at their interface. For example, the interface assembly 80 may include a seal such as an O-ring between the window 84 and the body 82. The window 84 and/or the aperture 86 may permit light to travel through the interface assembly 80, for example, between the sample and the objective 102 of the head assembly 70. The optoelectronic assembly 90 may be coupled to the body 82 such that the objective 102 of the head assembly 70 is a specified distance or range of distances from the optoelectronic assembly 90.

Figure 6A:
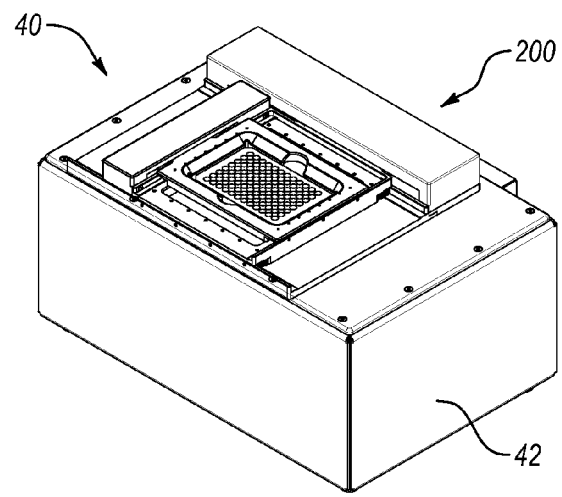
FIG. 6A is a perspective view of a non-limiting embodiment of the system of FIGS. 2A-2B with a device configured to analyze one or more samples positioned in a sample tray.
Figure 6B:
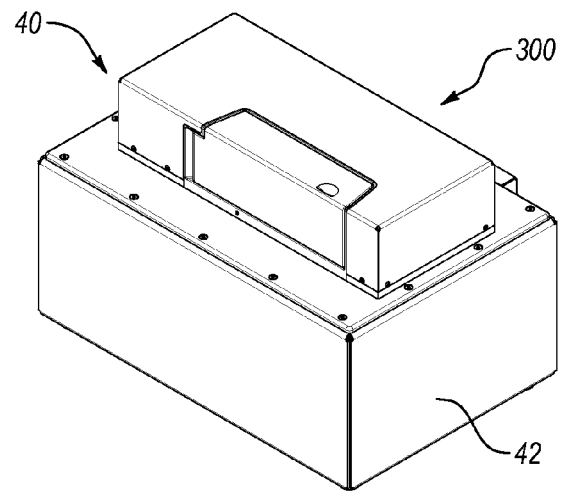
FIG. 6B is a perspective view of a non-limiting embodiment of the system of FIGS. 2A-2B with a device configured to analyze layers of analytes.
Figure 6C:
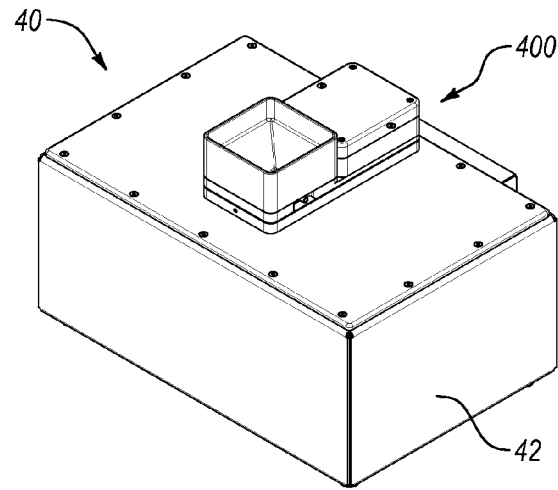
FIG. 6C is a perspective view of a non-limiting embodiment of the system of FIGS. 2A-2B with a device configured to analyze granular samples.

FIGS. 6A-6C illustrate the system 40 with different example configurations to process samples of different types and/or by different methods or techniques. FIG. 6A illustrates the system 40 with a device 200 configured to analyze one or more samples positioned in a sample tray. FIG. 6B illustrates the system 40 with a device 300 configured to analyze layers of samples, for example pills, tablets, capsules, medication, pellets, and/or other substances. FIG. 6C illustrates the system 40 with a device 400 configured to analyze particle samples such as powders, granules, and/or other substances. The system 40 may also be configured to analyze fluid samples such as liquids, gels, gases, and/or other substances. In such configurations, the system 40 may include an interface assembly 80 adapted to receive, deliver, process and/or analyze liquids, gels, gases, and/or other substances.

As mentioned above, the system 40 may be modular to permit the system 40 to be configured to analyze or process different types of samples. Additionally or alternatively, the system 40 may be modular to permit the system 40 to be configured to analyze or process samples by one or more different methods or techniques. Specifically, the interface assembly 80 may interface with modular components and/or devices. The modular components and/or devices may be configured to process, prepare and/or deliver analytes or samples over the window 84 to be analyzed by the system 40. The modular components and/or devices may include configurations suited for processing a specific type of sample or analyzing samples by a specific method or process. Additionally or alternatively, the modular components and/or devices may be configured to process samples either before or after they are analyzed, or both. For example, the modular components and/or devices may prepare the samples to be analyzed by the system 40. In another example, the modular components and/or devices may sort and/or separate samples after the samples are analyzed, for example, based on information obtained when the samples were analyzed.

Figure 7A:
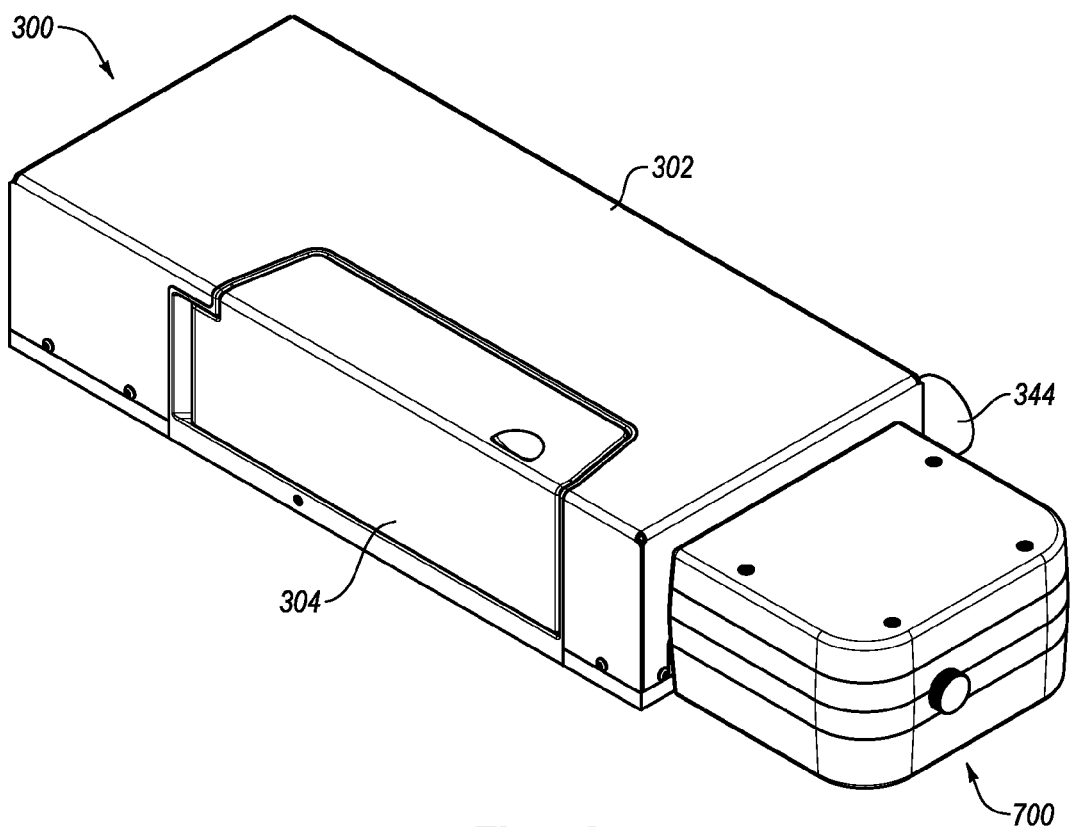
FIGS. 7A-7B are perspective views of the non-limiting embodiment of the device of FIG. 6B.
Figure 7B:
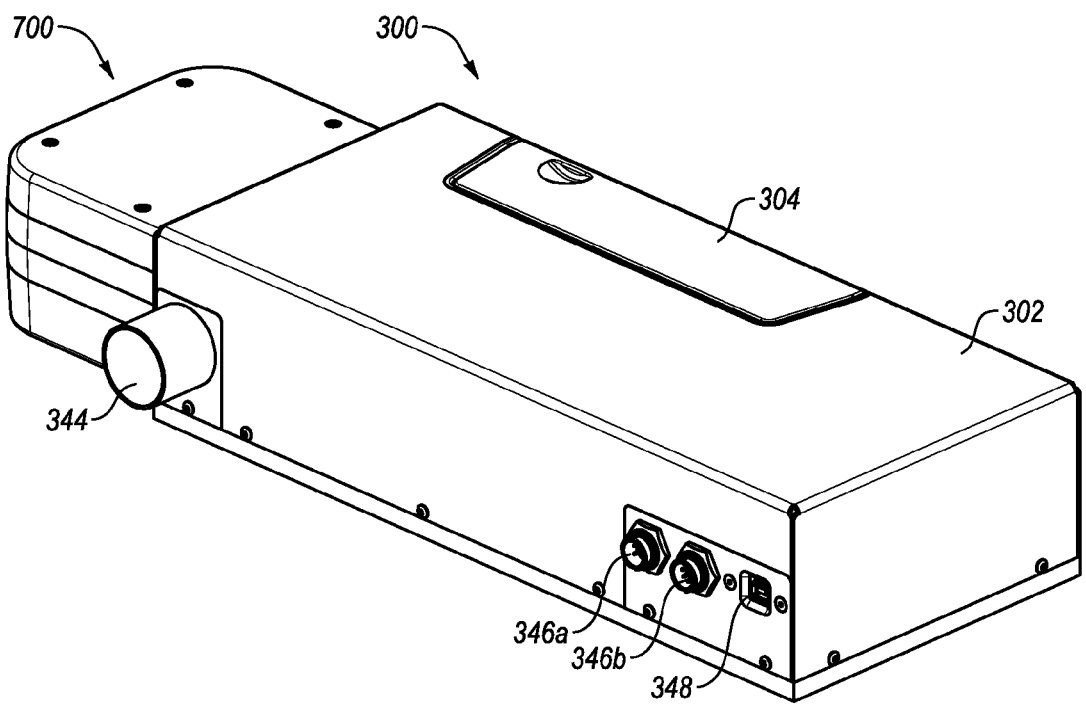

With attention to FIGS. 7A-7J and 8A-8E, the device 300 will be described in further detail. FIGS. 7A and 7B are perspective views of the device 300 for analyzing layers of analytes. As illustrated, the device may include a housing 302 surrounding at least a portion of the device 300. A door 304 configured to permit access to the interior of the housing 302 is positioned over a portion of the device 300. A filtering device 700 may be coupled to the device 300. The filtering device 700 will be described in further detail with respect to FIGS. 9A-9F.

As illustrated in FIG. 7B, the device 300 may include various connectors 344, 346a, 346b, and 348. The connectors 344, 346a, 346b, and 348 may connect portions of the device 300 inside of the housing 302 to other portions of the system 40. The connector 344 may be a fluid connector configured to be connected to, for example, a vacuum line, a fluid line and/or a gas line. The connector 344 may permit gaseous fluid to be evacuated from the device 300 and/or directed into the device 300. The connectors 346a, 346b, and 348 may be electronic connectors configured to transmit data, power and/or control signals. In some configurations, one of the connectors 346a, 346b may be coupled to corresponding connector 46 of the system 40 and/or the connector 348 may be coupled to corresponding connector 48 of the system 40.

In some configurations, one of the connectors 346a, 346b may couple the device 300 to other components of the system 40 to synchronize the other components with the device 300. For example, the device 300 may be coupled to a vacuum via a cable and the connector 346a. The vacuum may also be fluidly coupled to the device 300 via the fluid connector 344. The device 300 may operate the vacuum by transmitting power and/or control signals to the vacuum via the cable and the connector 346a. Specifically, the device 300 may activate the vacuum to remove materials via the fluid connector 344 as the device 300 is operating. The system 40 may be configured to synchronize the operation of the vacuum with the operation of the device 300, for example, by periodically activating the vacuum when removal of material is desired.

Figure 7C:
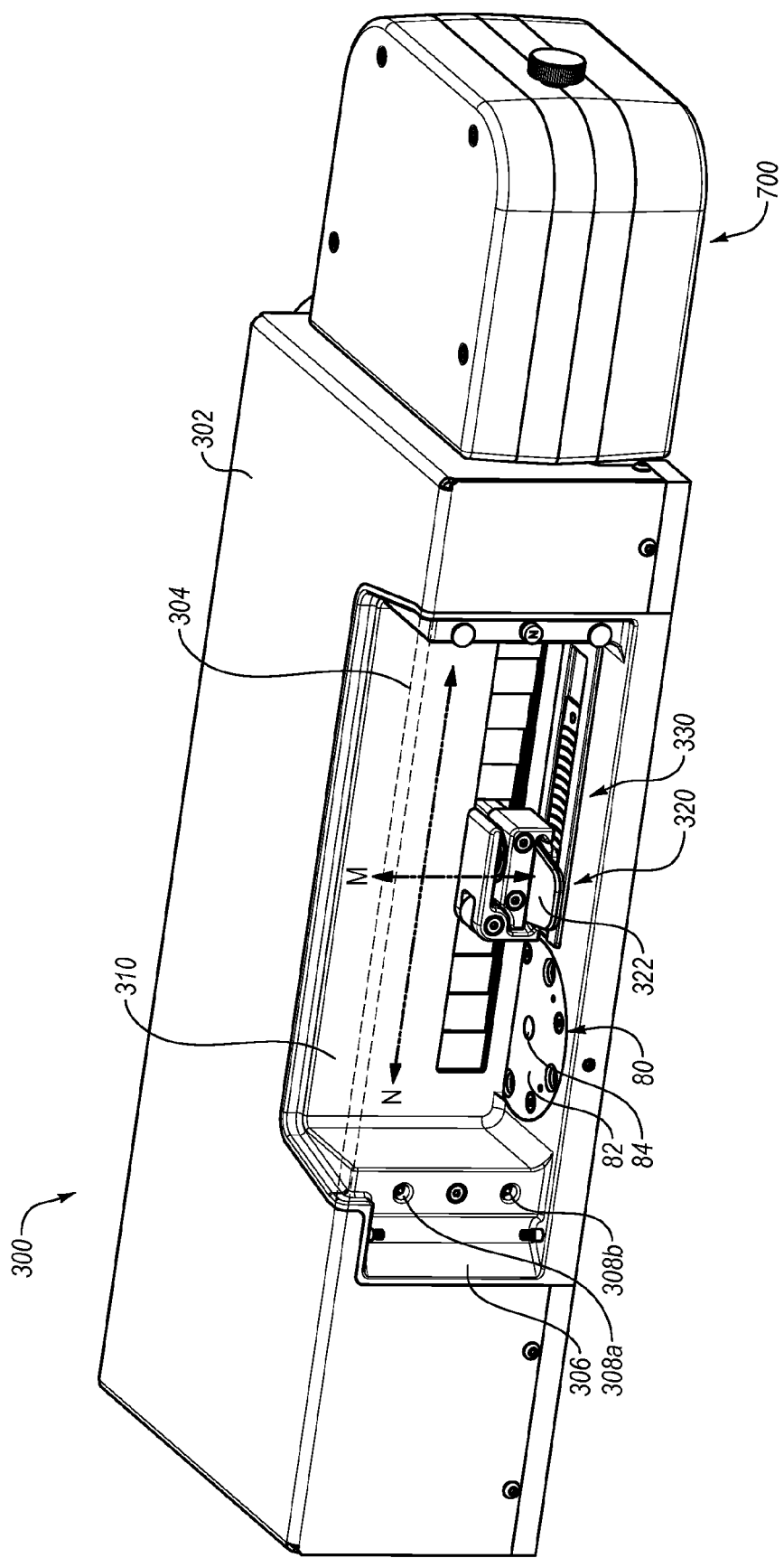
FIG. 7C is a perspective view of a portion of the device of FIG. 7A.

FIG. 7C illustrates the device 300 with the door 304 indicated by dashed lines to permit a view of a portion of the interior of the device 300. As illustrated, the device may include an interior barrier 310 separating portions of the interior of the device 300. The door 304 and the interior barrier 310 may define a portion of the device 300 that is accessible to a user. The accessible portion of the device may permit the user to operate the device 300.

As illustrated, the door 304 may be hingedly connected to the housing via a hinge 306. The hinge 306 may permit the door 304 to swing open laterally with respect to the housing 302. The portion of the device 300 that is accessible to a user when the door 304 is open may include a mandrel subassembly 320, a paring subassembly 330, and at least a portion of the interface assembly 80. Specifically, as illustrated, a portion of the interface assembly 80 with the window 84 and a top portion of the body 82 may be accessible to a user when the door 304 is in an open position.

In the illustrated configuration, the device 300 is configured to move the mandrel subassembly 320 along two axes M and N. For example, the device includes an actuation subassembly 380, which is described in further detail with respect to FIGS. 7G and 7H. The mandrel subassembly 320 may include a mandrel 322 configured to retain an analyte such as pills, tablets, capsules, medication, pellets, and/or other substances. The device 300 may be configured to move the mandrel subassembly 320 in directions of movement M and N to analyze and/or process the analyte. In operation, the device 300 may pare portions of the analyte by the paring subassembly 330 to expose a surface of the analyte. The exposed surface of the analyte may be positioned over the window 84 to analyze and/or process the analyte by the head assembly 70 via the interface assembly 80. Aspects of the operation of the device 300 will be described in further detail with respect to FIGS. 8A-8E.

The interior barrier 310 may include a channel occluded by partition members 390. The channel may permit the mandrel subassembly 320 to be moved in directions of movement M and N. The partition members 390 may be movably interlocked with one another to prevent material from passing from the accessible portion of the device 300 to the interior portion, or vice versa, as the mandrel subassembly 320 is moved.

The device 300 may include detectors 308a and 308b configured to detect whether the door 304 is an open or a closed position. The detectors 308a and 308b may be part of an interlock mechanism configured to disable operation of portions of the system 40 when the door 304 is open. For example, the interlock mechanism may disable emitters such as the emitters 96 of the interface assembly 80 and/or the emitter assembly 62 inside of the housing 42. In another example, the interlock mechanism may disable the movement of the mandrel subassembly 320. For example, the interlock mechanism may disable the movement of the mandrel subassembly 320 along the M and N axes.

Figure 7D:
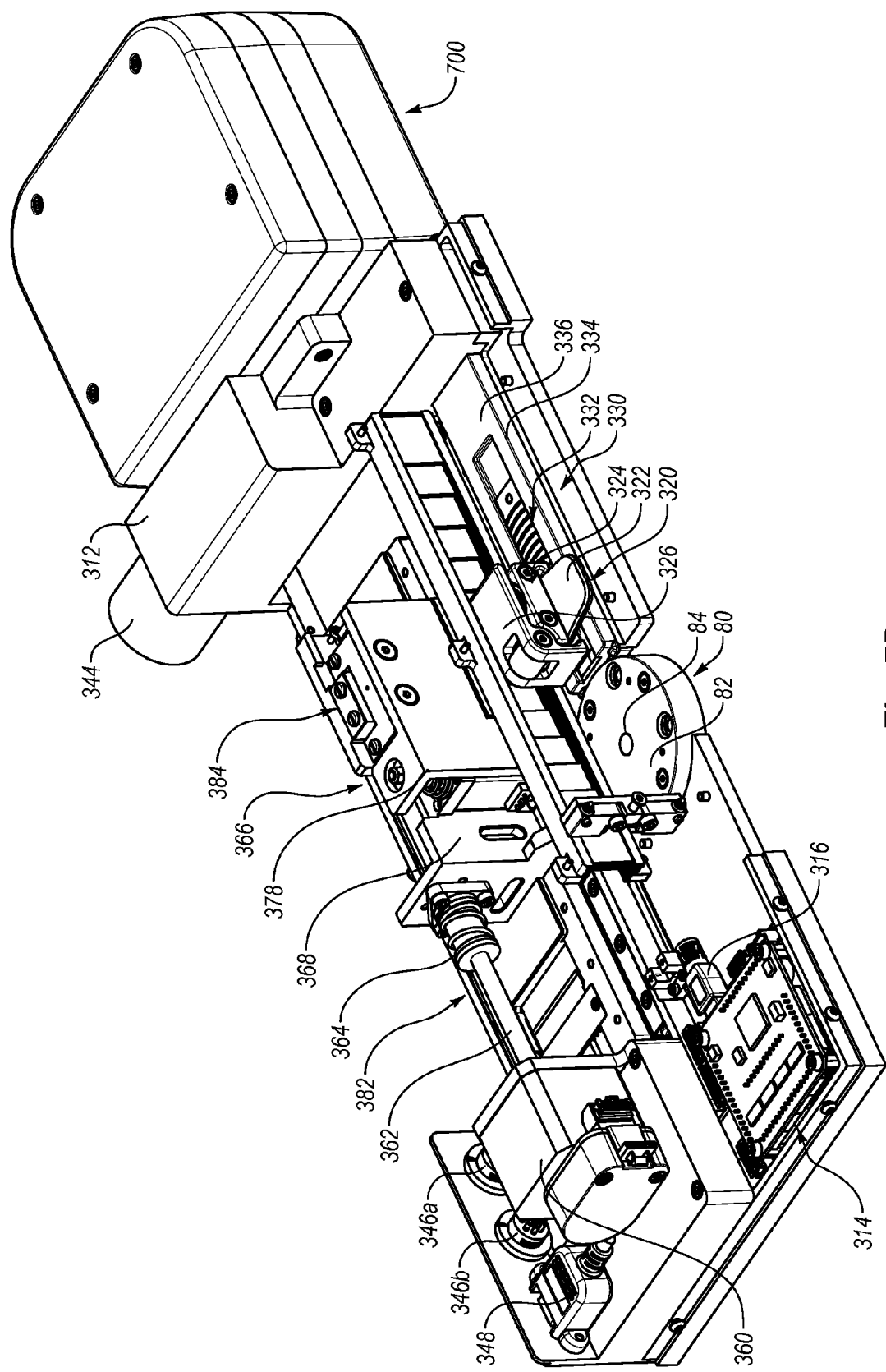
FIGS. 7D-7F are views of a portion of the device of FIG. 7A.
Figure 7E:
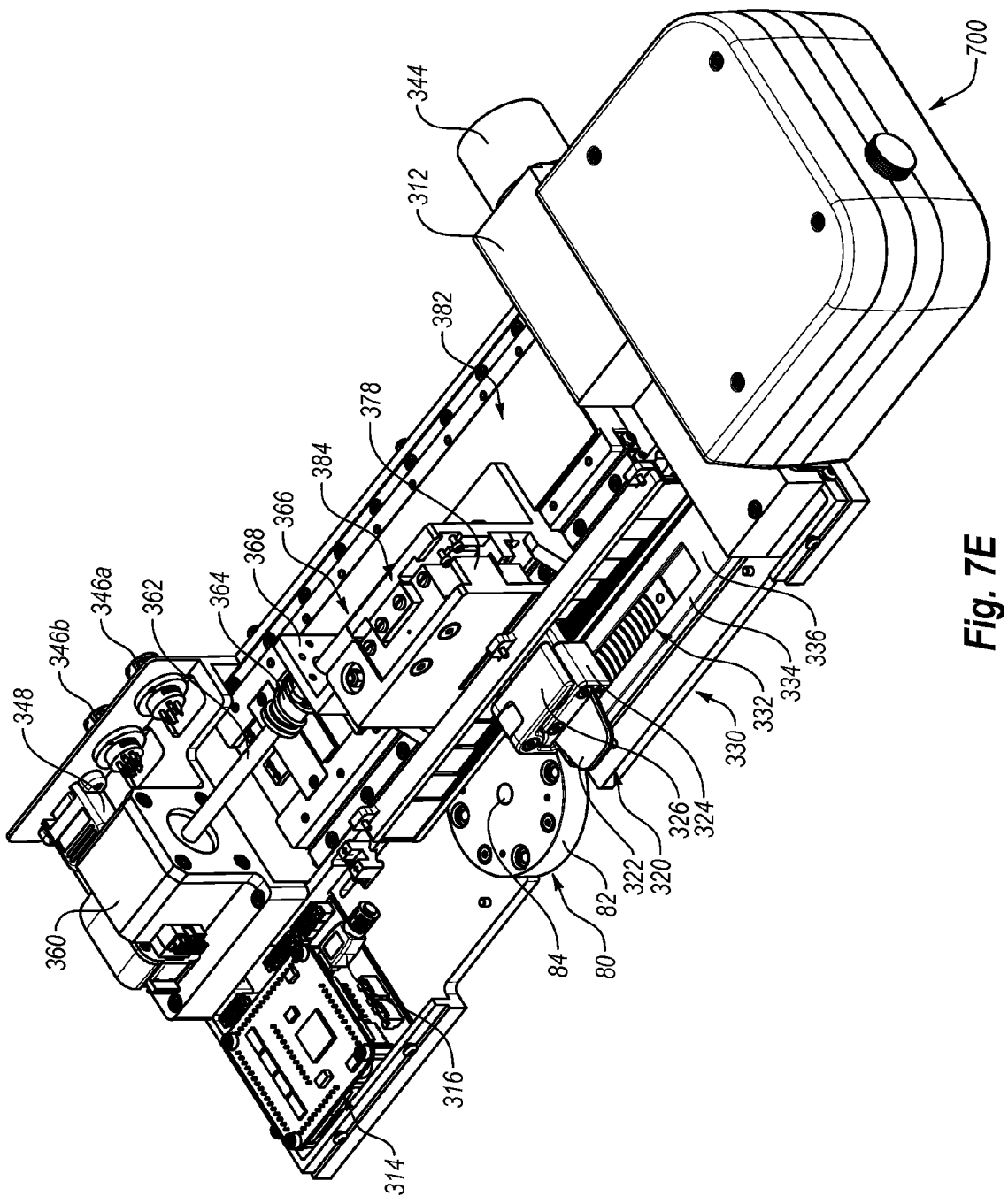
Figure 7F:
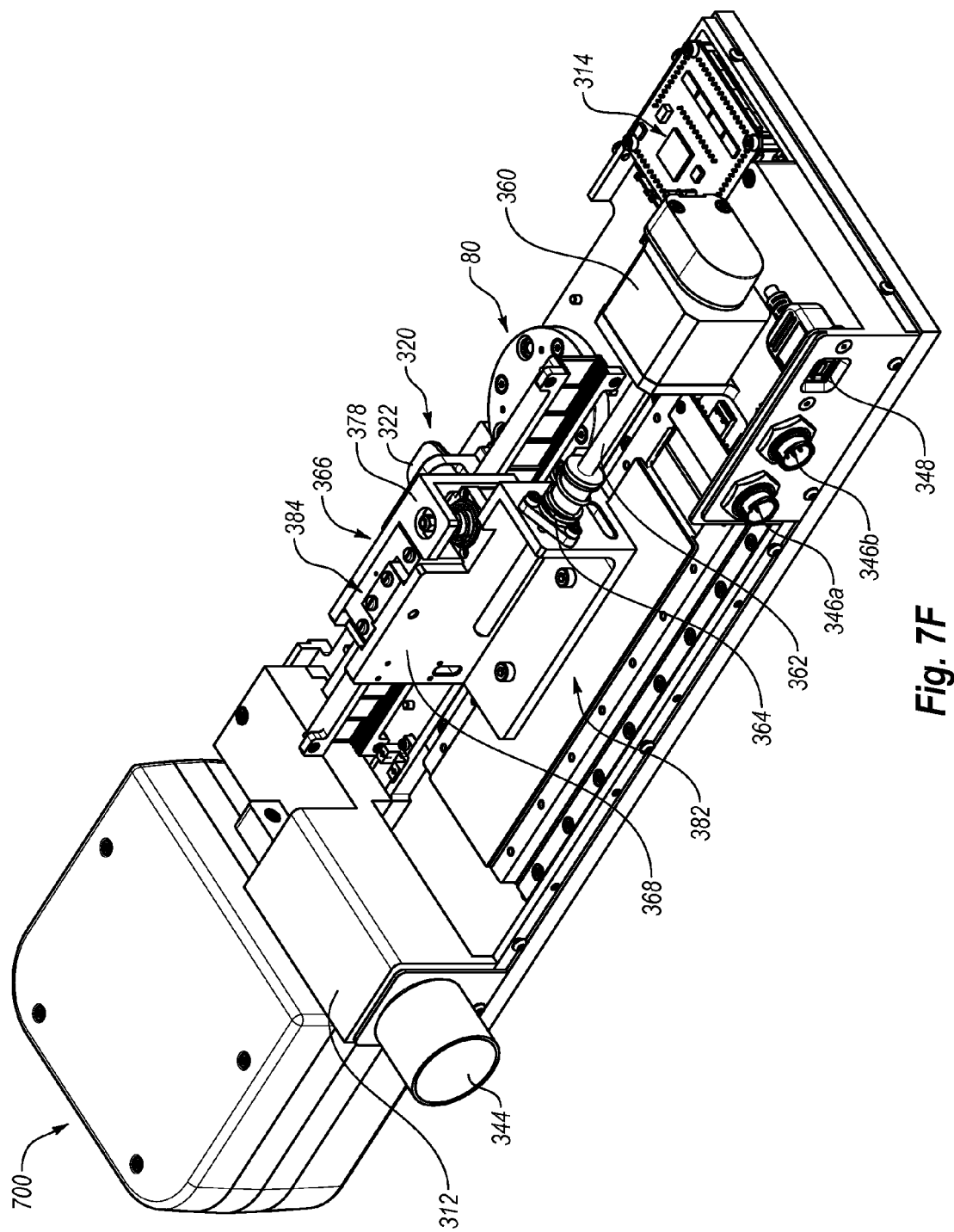

FIGS. 7D-7F illustrate the device 300 with the housing 302, the door 304, and the interior barrier 310 not shown to permit a view of the interior of the device 300. As illustrated, the mandrel subassembly 320 may include a mandrel holder 324 and a mandrel clamp 326 configured to removably secure and/or retain the mandrel 322.

The mandrel 322 may be configured to retain an analyte (for example, see analyte 350 illustrated in FIGS. 7J and 8A-8E) such as a pill, tablet, capsule, medication, pellet, and/or other substances. The analyte may be removably or non-removably secured to the mandrel 322. For example, an analyte may be adhered and/or glued to the mandrel 322. In another example, an analyte may be mechanically secured and/or fastened to the mandrel 322. In some configurations, the mandrel 322 may include a receptacle dimensioned and shaped to receive and/or secure an analyte with specific dimensions, ranges of dimension, and/or shapes. The mandrel 322 may be configured to retain analytes of different shapes and sizes. In some aspects, the mandrel 322 may universally fit many types of analytes that fall within a range of characteristics. In some configurations, the mandrel 322 may include retaining members that facilitate fixing analytes to the mandrel 322. Examples of retaining members include ridges, protrusions, textured surfaces, or other structures that facilitate fixing analytes to the mandrel 322.

In some configurations, the mandrel 322 may be formed, for example, of injection molded plastic. The mandrel 322 may be disposable and/or consumable. In some configurations where the mandrel 322 is disposable and/or consumable, the paring process may pare the analyte along with portions of the mandrel 322.

The paring subassembly 330 may include a housing 334 defining a chamber and one or more paring members 332. The paring members 332 may be surfaces and/or edges configured to pare an analyte such as a pill, tablet, capsule, medication, pellet, and/or other substances retained by the mandrel 322. The paring members 332 may be sized and shaped to remove layers of the analyte to expose underlying surfaces of the analyte. As illustrated, the housing 334 of the paring subassembly 330 may include openings into the chamber in between the paring members 332. The openings may be positioned in between the paring members 332 to permit remnants of at least portions of the pared layers of the analyte to enter the chamber. In some configurations, the paring members 332 may be formed of stainless steel or another suitable material.

The housing 334 may be configured to removably and/or non-removably secure and/or retain the paring members 332. The paring members 332 may be removably or non-removably secured to the housing 334. For example, the paring members 332 may be adhered and/or glued to the housing 334. In another example, the paring members 332 may be mechanically secured and/or fastened to the housing 334. In some configurations, the housing 334 may include a receptacle dimensioned and shaped to receive and/or secure the paring members 332. In some configurations, the housing 334 may be formed, for example, of injection molded plastic. The paring subassembly 330 may be disposable and/or consumable.

The device 300 may include a fluid conduit 336 fluidly coupling the paring subassembly 330 to the filtering device 700. The fluid conduit 336 may be configured to permit gaseous fluid to be evacuated from the chamber defined by the housing 334. A fluid conduit 312 may fluidly couple the connector 344 and the filtering device 700. When the connector 344 is connected to a vacuum line or vacuum device, substances may be evacuated from the chamber defined by the housing 334 via the filtering device 700. In such configurations, the filtering device 700 may remove at least a portion of the substances travelling through the filtering device 700 and exiting via the connector 344. For example, the removed substances may include solids or particulates. Such configurations may decrease or eliminate fouling of the vacuum line or vacuum device by evacuated substances because the evacuated substances are removed by the filtering device 700. In some configurations, the evacuated substances may include solids or particulates caused by shaving or paring of the analyte.

In operation, substances and/or particles pared off from an analyte by the paring members 332 may travel into the chamber defined by the housing 334. The substances and/or particles may then be evacuated by the vacuum line connected to the first connector 344 via the fluid conduit 336, the filtering device 700 and the fluid conduit 312.

In configurations where the paring subassembly 330 is disposable, the fluid conduits 312, 336 and/or the filtering device 700 may not be included. In such configurations, substances and/or particles pared off from an analyte by the paring members 332 may travel into the chamber defined by the housing 334. The substances and/or particles may then be disposed of with the disposable paring subassembly 330. In other configurations, both the paring subassembly 330 and the filtering device 700 may be disposable. In such configurations, substances and/or particles pared off from an analyte by the paring members 332 may be collected in the filtering device 700. The substances and/or particles may then be disposed of with the disposable filtering device 700 and/or the disposable paring subassembly 330.

Figure 7G:
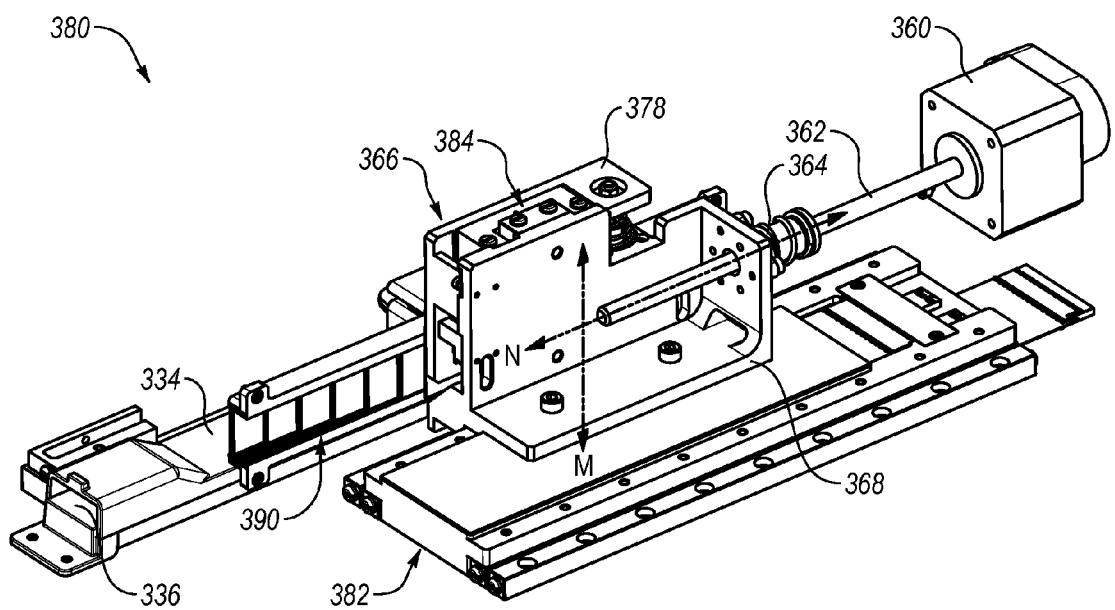
FIGS. 7G-7J are perspective views of portions of the device of FIG. 7A.
Figure 7H:
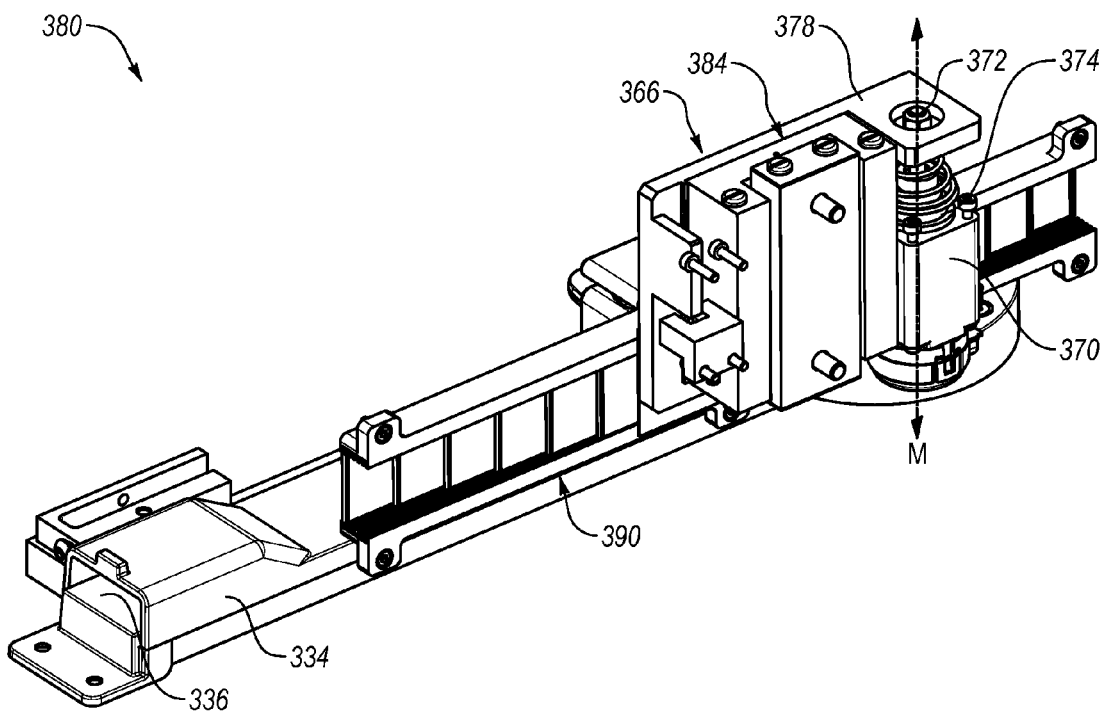

FIGS. 7G and 7H illustrate a portion of the device 300 including the actuation subassembly 380. As mentioned above, the device 300 includes the actuation subassembly 380 configured to move a mandrel subassembly 320 along two axes M and N. As illustrated, the device 300 may include one or more linear actuators or motors 360, 370. If the motors 360, 370 are rotational motors, each of the motors 360, 370 may be coupled to a corresponding lead screw 362, 372 configured to translate rotational motion to linear motion. If the motors 360, 370 are configured to convey linear motion, the lead screws 362, 372 may be shafts, coupling members, and/or omitted altogether. The lead screws 362, 372 may be coupled to corresponding anti-backlash members 364, 374.

As illustrated, the lead screw 362 may be coupled to a first member 368 of a mount subassembly 366. The lead screw 362 may be configured such that the motor 360 can drive the first member 368 along the axis N. As illustrated for example in FIG. 7F, the first member 368 of the mount subassembly 366 may be movably and/or slidingly coupled to the device 300 by a slide 382 configured to permit the first member 368 to move along the axis N.

Turning to FIG. 7H, additional details of the actuation subassembly 380 and the mount subassembly 366 will be described in further detail. The mount subassembly 366 may include a second member 378 that is configured to move along the axis M with respect to the first member 368. Specifically, the second member 378 may be movably and/or slidingly coupled to the first member 368 by a slide 384 configured to permit the second member 378 to move along the axis M. The lead screw 372 may be coupled to the second member 378 such that the motor 370 can drive the second member 378 along the axis M. As illustrated for example in FIG. 7E, the mandrel subassembly 320 may be coupled to the second member 378. The configuration of the first member 368 and the second member 378 may permit the mandrel subassembly 320 to be moved along one or both of the axes M and N.

Although the illustrated device 300 is configured to move the mandrel subassembly 320 along two directions of movement M and N, other configurations are also contemplated. For example, the device 300 may be configured to move the mandrel subassembly 320 along more or less than the two directions of movement M and N. Although the directions of movement M and N may be linear along axes orthogonal to one another, as illustrated, in some configurations the directions of movement may not be orthogonal to one another. Furthermore, the directions of movement M and N may be non-linear, for example, angular or arcuate.

As illustrated for example in FIGS. 7D-7F, the device 300 may include an electronic assembly 314 with one or more connectors 316. The electronic assembly 314 may include a controller configured to control the operation of at least a portion of the device 300. The connector 316 may be an electronic connector configured to transmit data, power, feedback, and/or control signals. In some configurations, the connector 316 may be coupled to the connector 348 to be coupled to other portions of the system 40. The electronic assembly 314 may include connectors electrically coupled to corresponding connectors of the motors 360, 370. The electronic assembly 314 may be configured to distribute power and/or control signals to other components of the device 300, such as the motors 360, 370. The electronic assembly 314 may be configured to receive data signals and/or feedback from the motors 360, 370. The electronic assembly 314 may be configured to receive power and/or control signals from other portions of the system 40, and/or may distribute such power and/or control signals to portions of the device 300. The electronic assembly 314 may be configured to operate the interlock for the door 304 of the device 300 (see for example FIGS. 7A and 7B). In some configurations, the electronic assembly 314 may operate and/or control other portions of the system 40, for example, a vacuum fluidly and electrically coupled to the device 300 and configured to move or evacuate substances.

Figure 7I:
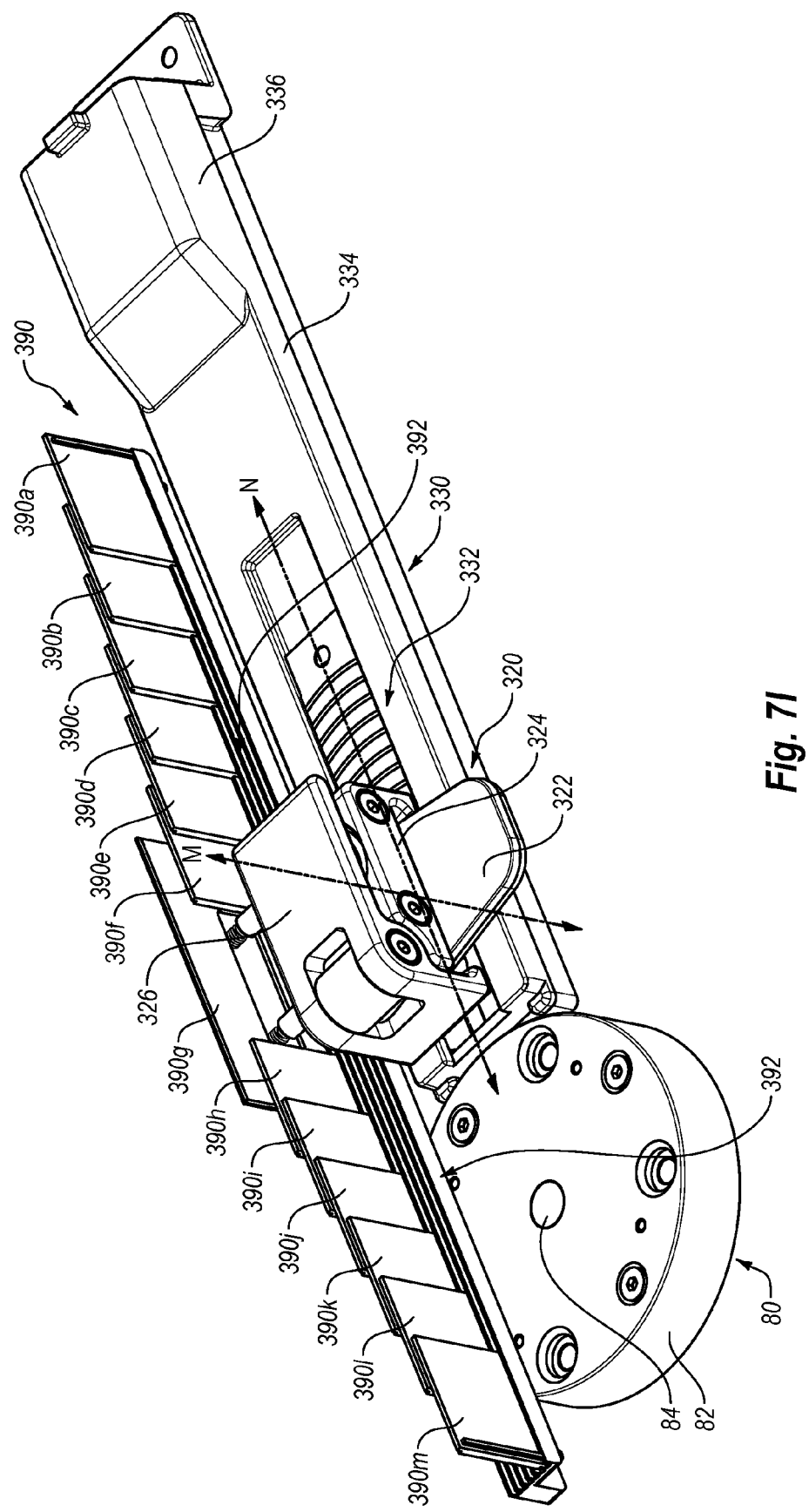

Turning to FIG. 7I, the partition members 390 will be described in further detail. As illustrated, the device 300 may include interlocked partition members 390a-m. Each partition member 390a-m may be movably positioned in channels 392 that permit the partition members 390a-m to slide along the N direction. Each partition member 390a-m may also include an interlocking feature such as a lip or protrusion that permits the partition member 390a-m to interlock with an adjacent partition member 390a-m. One of the partition members 390g may be coupled to and move along with the mandrel assembly 320. The partition member 390a-m may be configured such that the partition member 390g may move along the M direction as well as the N direction. As the mandrel assembly 320 is moved, the mandrel assembly 320 or the partition member 390g may displace adjacent partition members 390f and/or 390h, thereby permitting movement of the mandrel assembly 320 while maintaining separation between portions of the device 300.

Figure 7J:
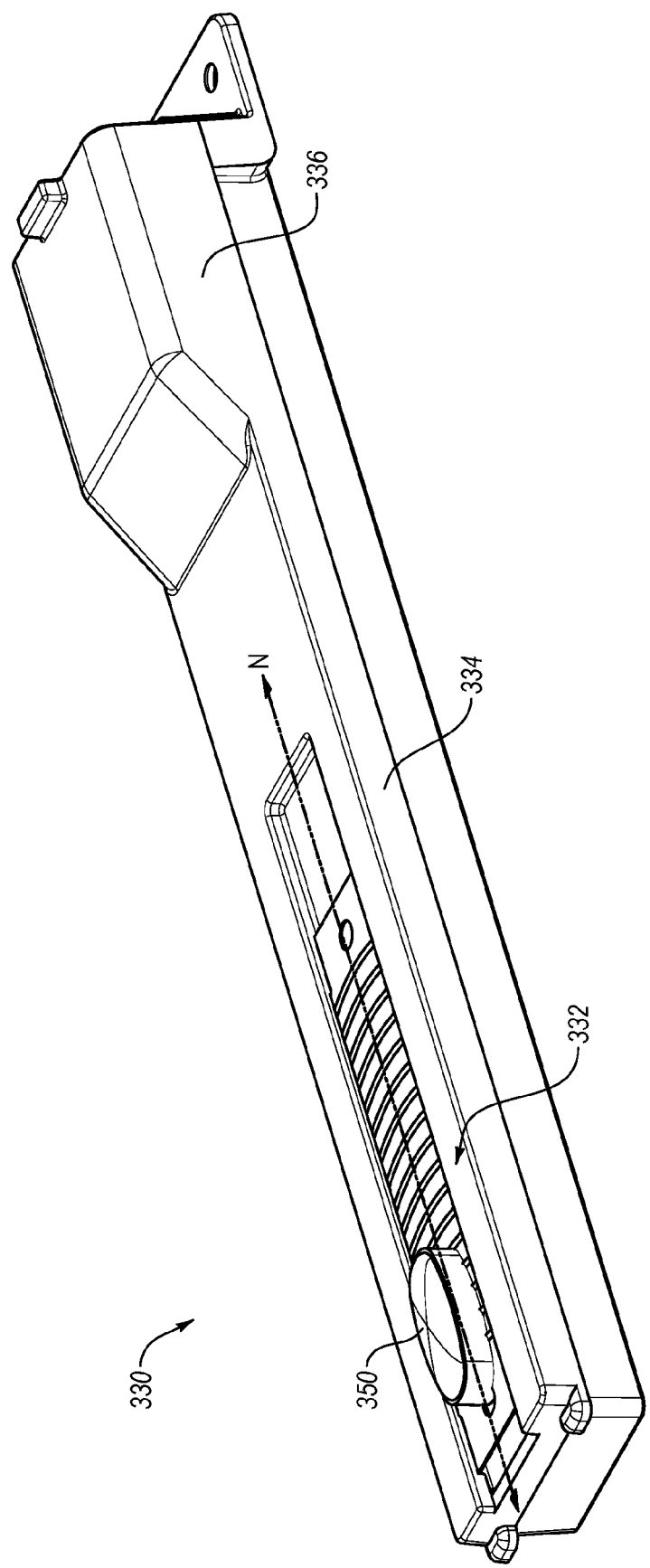

With attention to FIGS. 7I-7J and 8A-8E, analyzing and/or processing of analytes by the device 300 will be described in further detail. FIG. 7I illustrates the interface assembly 80, the mandrel subassembly 320 and the paring subassembly 330 in further detail. FIG. 7J illustrates an analyte 350 that may be retained by the mandrel 322 of the mandrel subassembly 320 (not shown in FIG. 7J). FIGS. 8A-8E illustrate side views of the analyte 350.

As illustrated in FIG. 7I, the mandrel subassembly 320 may be positioned such that the analyte 350 is at least partially positioned against the paring members 332. The mandrel subassembly 320 with the analyte 350 may then be moved in the N direction and move the analyte 350 in the N direction against the paring members 332.

Figure 8A:
Figure 8B:
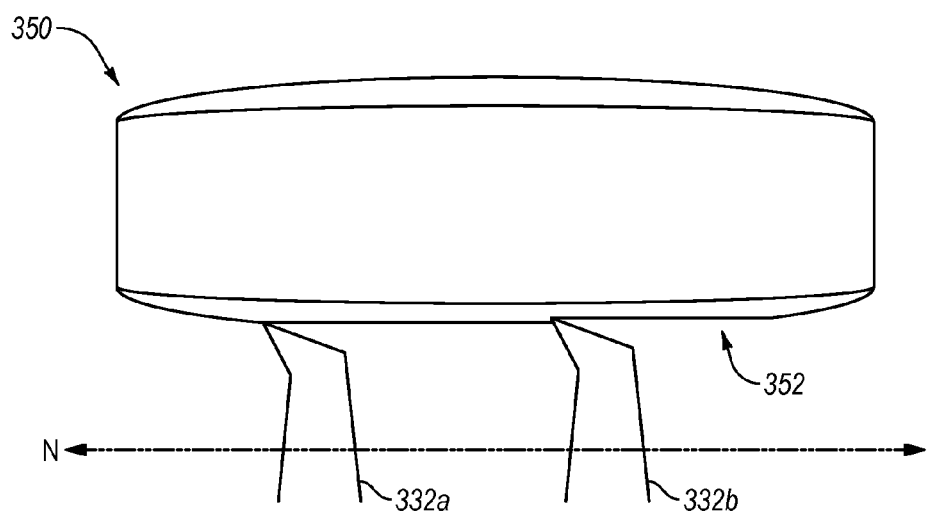

FIG. 8A illustrates the analyte 350 in further detail. As mentioned, the analyte 350 may be a pill, tablet, capsule, medication, pellet, and/or other substances. As illustrated in FIG. 8B, the analyte 350 may be moved with respect to paring members 332a and/or 332b to pare portions of the analyte 350 off to reveal a pared surface 352. As illustrated, each of the paring members 332a, 332b may remove a portion of the analyte 350. Accordingly, the paring members 332a, 332b may progressively remove portions of the analyte 350 off to reveal a pared surface 352.

The paring members 332a, 332b may represent two of the paring members 332 of the paring subassembly 330. As indicated by arrow N, either one or both of the analyte 350 and/or the paring members 332a, 332b may be moved with respect to one another to pare the analyte 350. In the configuration illustrated for example in FIGS. 7G-7I, only the analyte 350 moves with respect to the stationary paring members 332, however, other configurations may be implemented.

Figure 8C:
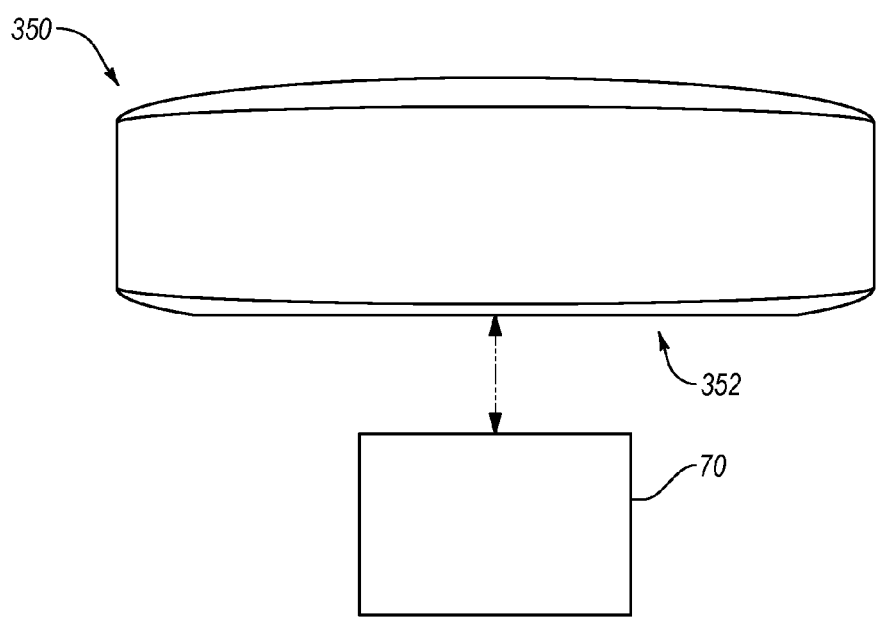

As the analyte 350 continues to be pared by the paring members 332a, 332b portions pared from the analyte 350 may form particles or portions that travel through the openings between the paring members 332a, 332b into the chamber defined by the housing 334 (see for example FIG. 7J). FIG. 8C illustrates the analyte 350 with a portion pared off revealing the entire pared surface 352.

Turning back to FIG. 7I for example, after a portion of the analyte 350 is pared, the mandrel subassembly 320 may move in the M direction away from the paring subassembly 330 to disengage the analyte 350 from the paring subassembly 330. The mandrel subassembly 320 may then move the analyte 350 in the N direction toward the interface assembly 80 and position the analyte 350 over the window 84. The mandrel subassembly 320 may then move in the M direction towards the window 84 to position the analyte 350 either against the window 84 or within a suitable distance (and/or range of distances) for the pared surface 352 of the analyte 350 to be analyzed and/or processed, for example, by the head assembly 70.

As illustrated for example in FIG. 8C, the pared surface 352 of the analyte 350 may be analyzed and/or processed by the head assembly 70. Analyzing and/or processing the pared surface 352 may include: the head assembly 70 directing electromagnetic radiation toward the pared surface 352 and/or receiving electromagnetic radiation from the pared surface 352 to obtain information regarding characteristics of the analyte 350.

Turning back to FIG. 7I for example, after the pared surface 352 is analyzed and/or processed by the head assembly 70, the mandrel subassembly 320 may move in the M direction away from the head assembly 70. The mandrel subassembly 320 may then move the analyte 350 in the N direction towards paring subassembly 330 and position the analyte 350 over paring members 332 of the paring subassembly 330. The mandrel subassembly 320 may then move the analyte 350 in the M direction toward the paring subassembly 330 and position the analyte 350 against at least one of the paring members 332. The mandrel subassembly 320 may then once again move the analyte 350 in the N direction against the paring members 332 to pare another portion from the analyte 350 to reveal another pared surface.

Turning to FIG. 8D, the process of paring a portion of the analyte 350 and analyzing and/or processing the pared surfaces may continue for a plurality of layers 358*a*-*n* of the analyte 350. The device 300 may be configured such that each of the layers 358*a*-*n* may include specified dimensions and/or ranges of dimensions, for example, thickness and/or height.

In some aspects, the dimension(s) of the removed layers may depend on characteristics of the analyte 350, such as the hardness of the analyte 350 or portions of the analyte 350. Additionally or alternatively, the dimension(s) of the removed layers may depend on characteristics of the paring members 332, such as sharpness or hardness, or the force or pressure applied between the paring members 332 and the analyte 350.

The dimensions of the layers 358*a*-*n* may depend on various characteristics of the device 300 such as its configuration and/or operation. For example, dimensions of the layers 358*a*-*n* may at least partially depend on the configuration of the paring members 332 such as the number of paring members 332, the shape, dimensions, sharpness, and/or hardness of one or more of the paring members 332. In another example, dimensions of the layers 358*a*-*n* may at least partially depend on the amount of force that is applied by the analyte 350 on one or more of the paring members 332, or vice versa. The dimensions of the layers 358*a*-*n* may at least partially depend on the amount of force that is applied by the mandrel subassembly 320. Additionally or alternatively, the dimensions of the layers 358*a*-*n* may depend on various characteristics of the analyte 350 such as hardness.

In some configurations, more than one of the layers 358*a*-*n* may be pared off prior to a surface being analyzed. In such configurations, not every surface of each of the layers 358*a*-*n* may be analyzed. In some configurations, a surface may be analyzed only after a certain amount of material is pared from the analyte 350.

In some configurations, the layers 358*a*-*n* may include at least one dimension between zero (0) and one hundred (100) microns, between two (2) and fifty (50) microns, and/or between any range of values spanning from zero (0) and one hundred (100) microns. In some configurations, the layers 358*a*-*n* may include at least one dimension between zero (0) and one hundred (100) microns, between two (2) and fifty (50) microns, and/or between any range of values spanning from zero (0) and one hundred (100) microns.

In some configurations, an adaptive algorithm may be used to achieve layers 358*a*-*n* with certain dimensions. For example, a layer may be substantially twenty (20) microns, fifty (50) microns, or five-hundred (500) microns. In some configurations, each paring member 332 may remove a portion of each of a layer to achieve a specified dimension of the layer. For example, if a layer is twenty (20) microns, each paring member 332 may remove two (2) microns to achieve a layer that has a dimension of substantially twenty (20) microns+/−two (2) microns. In another example, if a layer is fifty (50) microns each paring member 332 may remove five (5) microns to achieve a layer that has a dimension of substantially twenty (50) microns+/−five (5) microns. In yet another example, for a relatively larger layer with a dimension of five-hundred (500) microns, the paring members 332 may initially be configured to remove fifty (50) microns of material, and as the five-hundred (500) micron target approaches, the configuration of the paring members 332 may be modified to remove five (5) to ten (10) microns of material to achieve a layer with a dimension of five-hundred (500) microns+/−twenty (20) microns. In other configurations, the layers 358*a*-*n* may include greater or lesser dimensions and/or the paring members 332 may remove other dimensions of material.

For some analytes that may be analyzed and/or processed by the system 40 including the device 300, the analytes may include a coating surrounding at least a portion of the analytes. For example, some medications include coatings that are formed of a different substance than the rest of the medication. Turning to FIG. 7E, in some circumstances, portions 354*a*, 354*b*, 354*c*, 354*d* of the analyte 350 may include a coating or other surface feature. In some configurations, the analyzing and/or processing of the analyte 350 described above may facilitate obtaining information regarding the coating, such as its composition and/or dimensions. In other configurations, the composition and/or dimensions of a coating of the analyte 350 may be known or estimated. In such configurations, some or all of the portions 354*a*, 354*b*, 354*c*, 354*d* of the analyte 350 may be pared without being analyzed and/or processed, for example, by the head assembly 70.

Figure 9A:
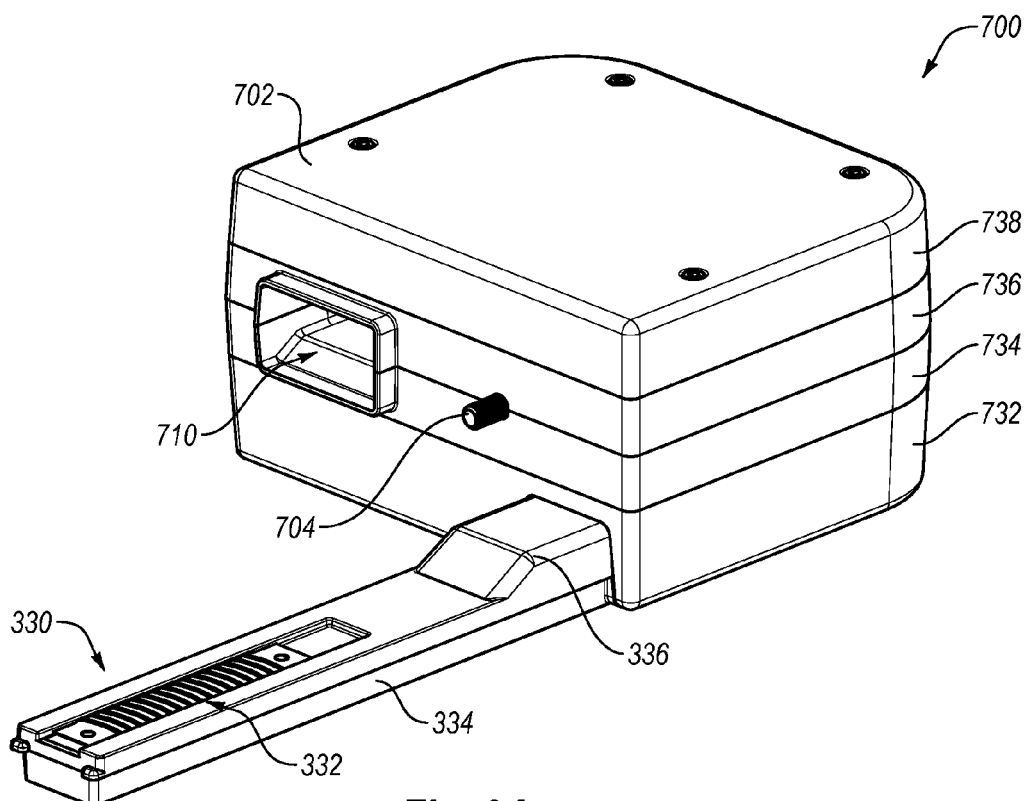
FIG. 9A is a perspective view of a non-limiting embodiment of a filtering device and a paring assembly.
Figure 9B:
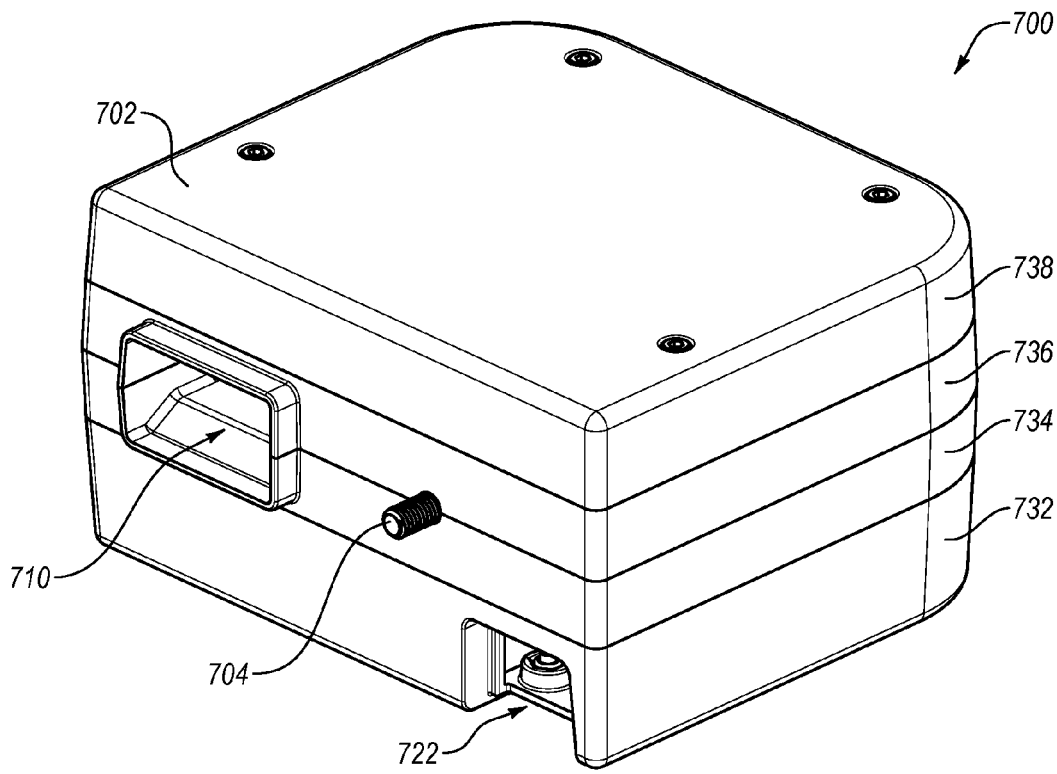
FIG. 9B is a perspective view of the filtering device of FIG. 9A.
Figure 9C:
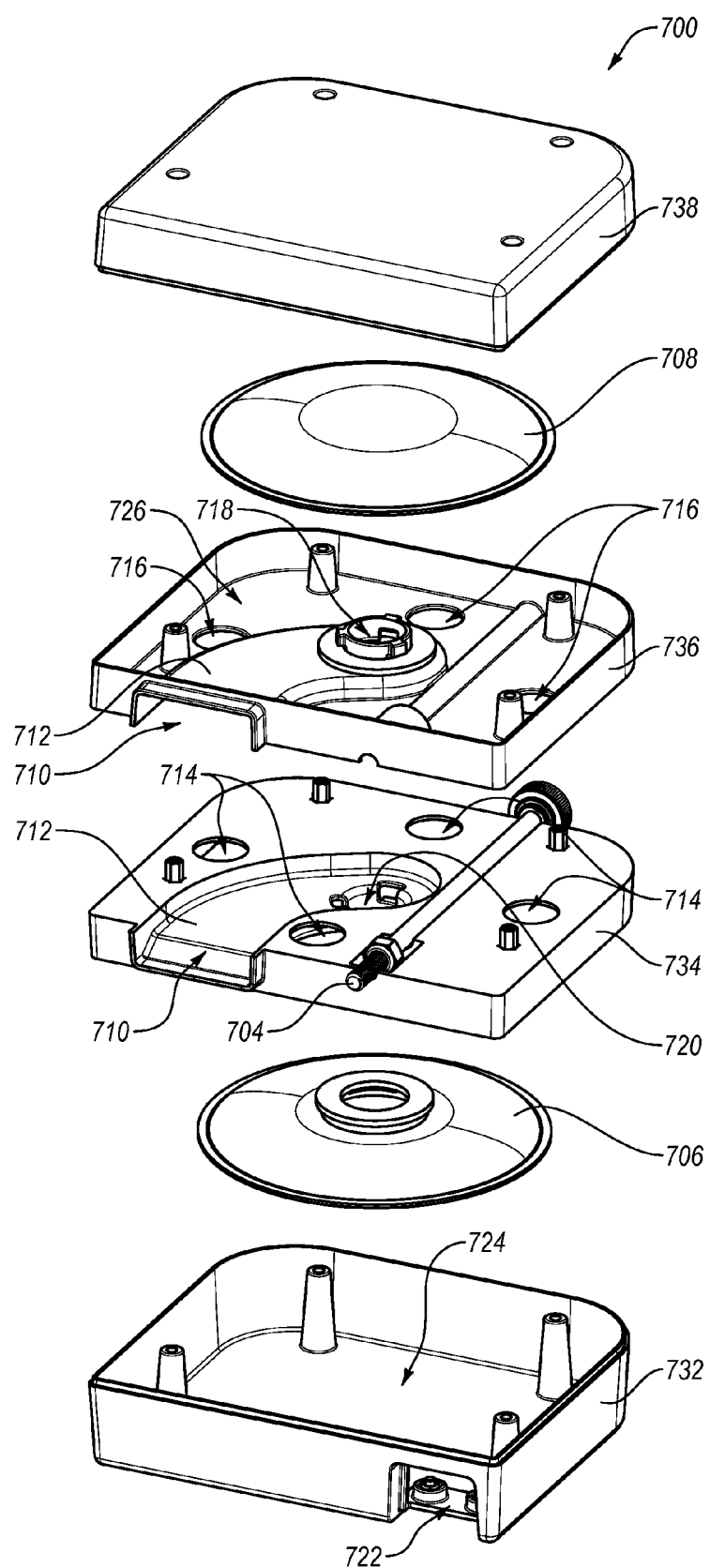
FIG. 9C is a top exploded view of the filtering device of FIG. 9A.
Figure 9D:
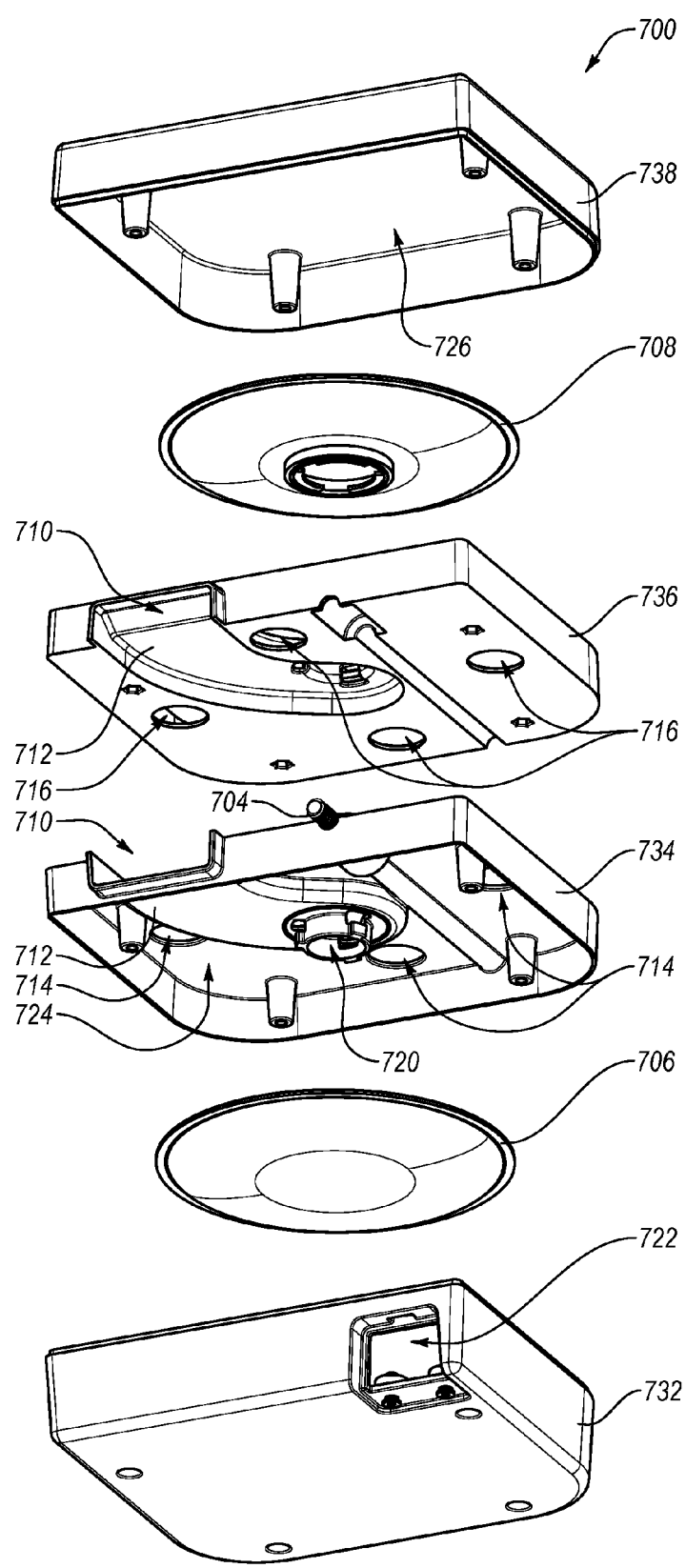
FIG. 9D is a bottom exploded view of the filtering device of FIG. 9A.
Figure 9E:
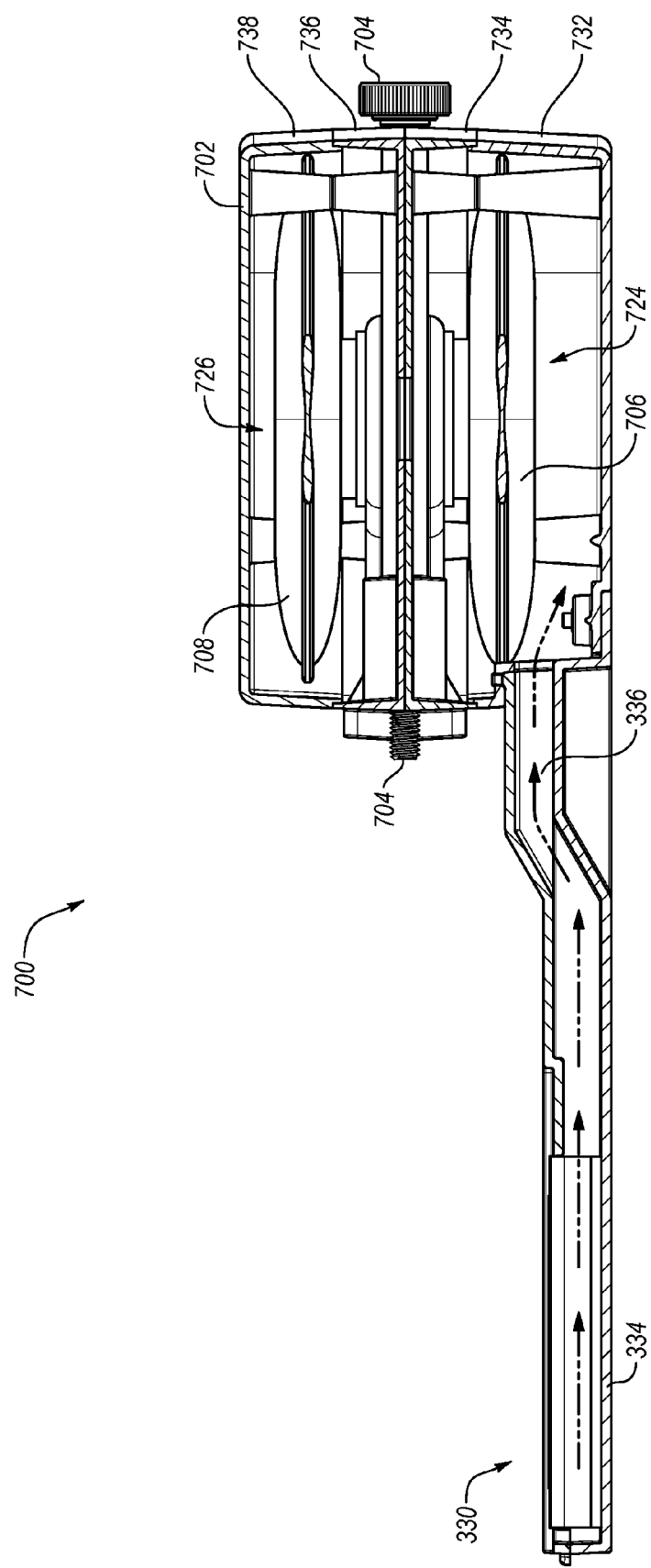
FIG. 9E is a side section view of the filtering device of FIG. 9A.
Figure 9F:
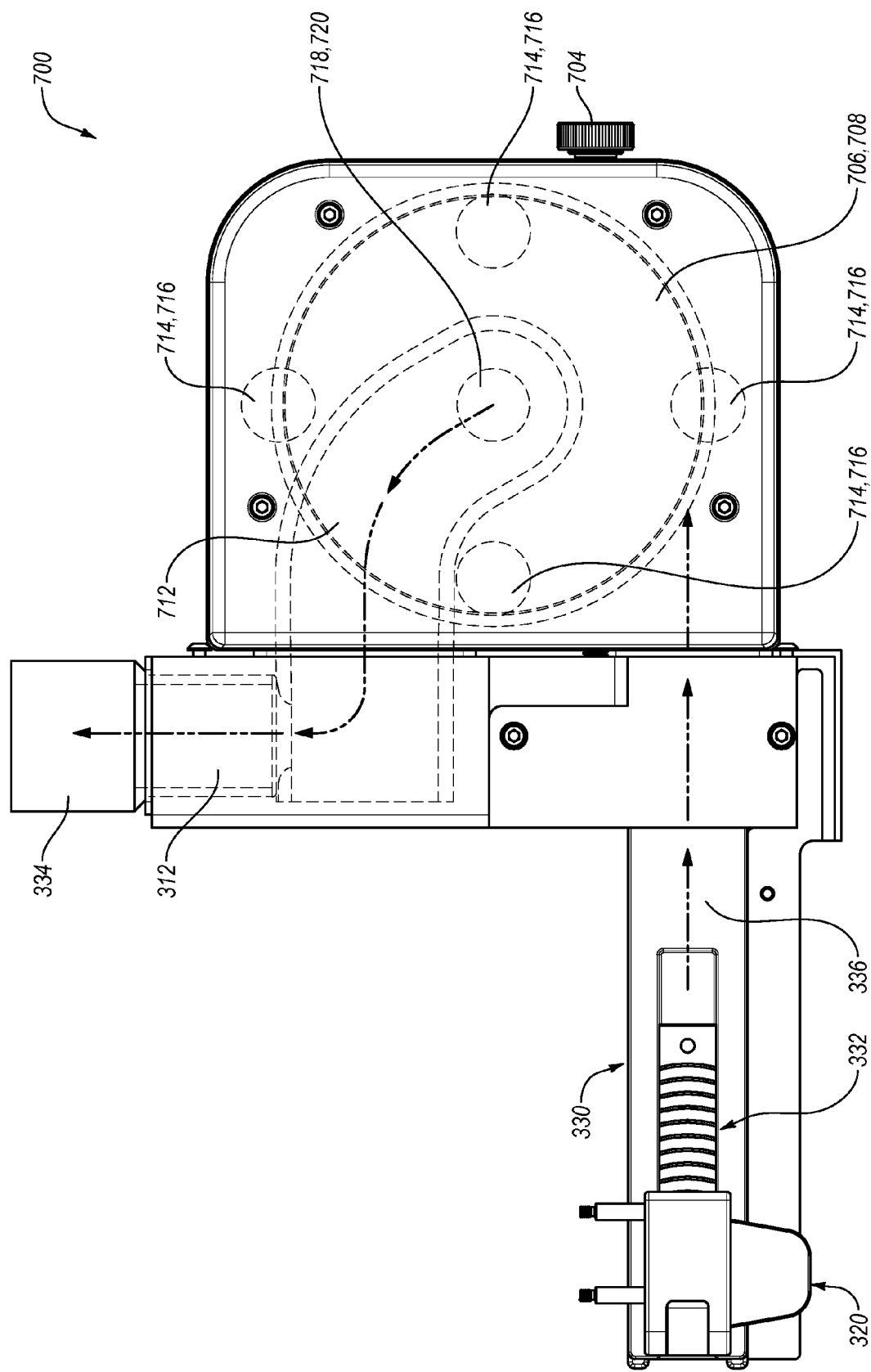
FIG. 9F is a top representation of the filtering device of FIG. 9A.

With attention to FIGS. 9A-9E, the filtering device 700 will be described in further detail. FIG. 9A is a perspective view of the filtering device 700 and the paring assembly 330. FIG. 9B is a perspective view of the filtering device 700 with the paring assembly 330 not shown. FIG. 9C is a top exploded view of the filtering device 700. FIG. 9D is a bottom exploded view of the filtering device 700. FIG. 9E is a side section view of the filtering device 700 and the paring assembly 330. FIG. 9F is a top representation of the filtering device 700, the paring assembly 330, and the mandrel assembly 320.

As illustrated in FIGS. 9A-9D, the filtering device 700 may include a housing 702 surrounding at least a portion of the filtering device 700. The housing 702 may be defined by body portions 732, 734, 736, 738 of the filtering device 700. As illustrated in FIG. 9A, the filtering device 700 may be coupled to the paring assembly 330. The filtering device 700 may be configured to separate and/or filter material evacuated from the chamber defined by the housing 334 of the paring assembly 330, as will be described in further detail below.

As illustrated in FIG. 9A, the body portion 732 may define an inlet 722 and the body portions 734 and 736 may define an outlet 710. The outlet 710 may be coupled to a vacuum source or fluid line to permit fluid and materials to be evacuate from the paring assembly 330 via the filtering device 700. Specifically, the outlet 710 may be fluidly coupled to the fluid conduit 312 and the connector 344 of the device 300 as illustrated for example in FIGS. 7D-7F. The inlet 722 may permit fluid and/or material from the paring assembly 330 to enter the filtering device 700.

Material may pass from the chamber defined by the housing 334 through the fluid conduit 336 and into the filtering device 700 via the inlet 722. In the illustrated configuration, the material from the paring assembly 330 may be displaced by flowing fluid driven by a vacuum source or fluid line. The filtering device 700 may separate and/or filter all or some of the material passing through the filtering device 700, as will be described in further detail below. In such configurations, fluid passing through the outlet 710 may be absent of the material or may include decreased quantities of the material. Accordingly, the filtering device 700 may decrease and/or prevent fouling of the vacuum source or fluid line. Additionally or alternatively, the filtering device 700 may prevent material from leaving the filtering device 700 and/or contaminating areas outside of the filtering device 700. For example, in some applications the analyte processed by the paring assembly 330 may be a hazardous material, and the filtering device 700 may prevent particles from the hazardous material from leaving and causing harm outside of the filtering device 700.

In some configurations, the filtering device 700 and the paring assembly 330 may form a single assembly that may be a filtered blade cartridge. In such configurations, the filtering device 700 and the paring assembly 330 may be integral to or permanently coupled to one another. The filtered blade cartridge may seal material shaved from an analyte inside of the housing 702. The filtered blade cartridge may be a disposable assembly or may be archived for future analyzation. In some configurations, a single filtered blade cartridge may be used for a specified number of analytes, such as specified amount of pills. In further configurations, a single filtered blade cartridge may be used for a specified type of analytes, such as a specific type of pill. In further configurations, a single filtered blade cartridge may be used to process a specified number of analytes based on: the hardness of the analytes; the sharpness of the paring members 332 of the paring assembly 330; the amount of analytes that may be processed before the filtering device 700 if fouled or full of material; to prevent cross-contamination; or any suitable combination thereof.

A coupling member 704 may be configured to couple the filtering device 700 and/or the paring assembly 330 to the device 300. In the illustrated configuration, the coupling member 704 extends through the housing 702 between the body portions 734, 736 and may be fastened to a portion of the device 300. The coupling member 704 may retain the filtering device 700 to the device 300 such that the outlet 710 is aligned with the fluid conduit 312, as illustrated for example in FIGS. 7D-7F.

In configurations where the filtering device 700 and the paring assembly 330 are a filtered blade cartridge, the paring assembly 330 may be positioned in a channel of the device 300 to align the paring assembly 330 with respect to the mandrel assembly 320, for example, in the directions M and N. In such configurations, the coupling member 704 may then be secured to the device 300 to fix the filtered blade cartridge to the device 300.

With attention to FIGS. 9C-9F, the interior of the filtering device 700 will be described in further detail. Although in the illustrated configuration the filtering device 700 includes four body portions 732, 734, 736, 738, the filtering device 700 may include any suitable number and/or configurations of body portions. As illustrated, the body portions 732 and 734 may define a chamber 724. Fluid that may include material may travel from the paring assembly 330 into the chamber 724 via the inlet 722. The body portions 736 and 738 may define a chamber 726. The body portion 734 may include openings 714 aligned with openings 716 of the portion 736. The aligned openings 714 and 716 may fluidly couple the chamber 724 with the chamber 726 such that fluid and/or material may travel between the chambers 724, 726.

The body portions 734 and 736 may define an outlet conduit 712 fluidly coupled to the outlet 710. The outlet conduit 712 may be fluidly coupled to the chamber 726 via an opening 718 defined in the body portion 736. Similarly, the outlet conduit 712 may also be fluidly coupled to the chamber 724 via an opening 720 defined in the body portion 734. A filter 706 may be positioned inside of the chamber 724 between the body portions 732 and 734 to occlude the opening 720. Similarly, a filter 708 may be positioned inside of the chamber 726 between the body portions 736 and 738 to occlude the opening 718. The filters 706, 708 may be configured to permit fluids such as gases to pass through while preventing particles and/or solids from passing through the filters 706, 708. Accordingly, the filters 706, 708 may permit fluid to flow through the filters 706, 708 into the outlet conduit 712 via the openings 718, 720, while separating materials such as particles and/or solids such that the particles and/or solids are collected in the chambers 724 and/or 726. In the illustrated configuration, the filters 706, 708 are coupled to corresponding body portions 736 and 734 via bayonet mount attachments that include a gasket, although other attachments may be employed in other configurations.

In some configurations, one or both of the filters 706, 708 may be: a respirator filter, a mechanical filter, high-efficiency particulate arrestance (HEPA) filter, P100 rated particle filter, or any other filter suitable for a desired application, or a combination thereof. In some configurations, one or both of the filters 706, 708 may be configured to: remove particles greater than 0.3 microns in size; filter at least 99.97% of airborne particles; filter at least 99% of airborne particles; filter by interception, impaction, diffusion, and/or other filtering mechanisms; or a combination thereof.

In operation, a vacuum source or fluid line may be coupled to the connector 344 of the device 300 thereby creating negative pressure through the filtering device 700 to evacuate fluid and material from the chamber defined by the housing 334 of the paring assembly 330. Fluid including the material may travel through the inlet 722 into the chamber 724. A portion of the fluid including the material may travel from the chamber 724 through the openings 718 and 720 into the chamber 726. The material in the fluid may be filtered by the filters 706, 708 and may be retained in the chambers 724 and/or 726. The fluid may flow through the filters 706, 708 into the outlet conduit 712 via the openings 718, 720. The fluid may continue through the outlet 710 and into the fluid conduit 312 of the device 300 and through the connector 344 coupled to a vacuum source or fluid line. In some aspects, the fluid may be absent of or substantially absent of solid material or particles.

Figure 10:
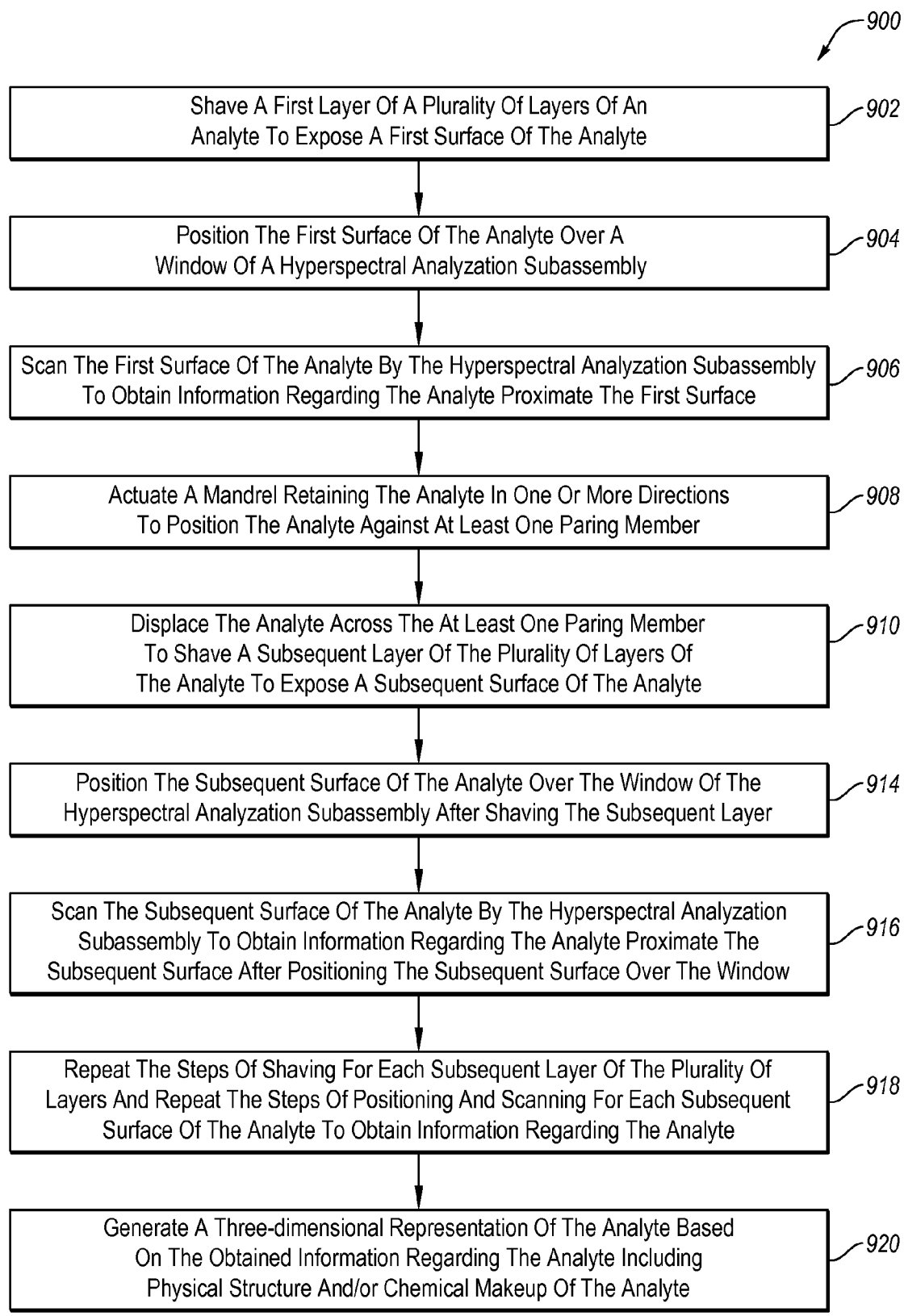
FIG. 10 illustrates an example configuration of a method.

With attention to FIG. 10, a method 900 of analyzing an analyte will be discussed in further detail. In some embodiments, the method 900 may be performed by a device corresponding to the device 300 of FIGS. 7A-7J and/or FIGS. 9A-9F. At step 902, a first layer of a plurality of layers of an analyte may be shaved to expose a first surface of the analyte.

In some configurations of the method 900, a paring subassembly includes a housing defining a chamber that receives remnants of at least a portion of the first layer removed from the analyte and the method 900 may include evacuating the chamber of at least the a portion of the first layer removed from the analyte. In some configurations, the material shaved off of the first layer may fall into the chamber defined by the housing. The material may be collected in the chamber defined by the housing and may be disposed or archived. Alternatively, the material may be evacuated from the chamber. For example, the material may be evacuated by a vacuum or fluid line. The material may be displaced through a filtering device, such as the filtering device 700 of FIGS. 9A-9F. The material collected in the filtering device may be disposed or archived.

At step 904, the first surface of the analyte may be positioned over a window of a hyperspectral analyzation subassembly. At step 906, the first surface of the analyte may be scanned by the hyperspectral analyzation subassembly to obtain information regarding the analyte proximate the first surface. At step 908, a mandrel retaining the analyte may be actuated in one or more directions to position the analyte against at least one paring member. At step 910, the analyte may be displaced across the at least one paring member to shave a subsequent layer of the plurality of layers of the analyte to expose a subsequent surface of the analyte.

At step 914, the subsequent surface of the analyte may be positioned over the window of the hyperspectral analyzation subassembly after the subsequent layer is shaved. At step 916, the subsequent surface of the analyte may be scanned by the hyperspectral analyzation subassembly to obtain information regarding the analyte proximate the subsequent surface, after the subsequent surface is positioned over the window. At step 918, the steps of shaving may be repeated for each subsequent layer of the plurality of layers and the steps of positioning and scanning may be repeated for each subsequent surface of the analyte to obtain information regarding the analyte proximate each of the subsequent surfaces. At step 920, a three-dimensional representation of the analyte may be generated based on the obtained information regarding the analyte including physical structure and/or chemical makeup of the analyte.

In some configurations, the method 900 may include obtaining visible light spectrum pictures and/or Raman spectrometer measurements of the pared surface of one or more of the plurality of layers. The method 900 may include processing the visible light spectrum pictures and/or Raman spectrometer measurements. The method 900 may include processing the data obtained about the analyte to form a three dimensional view of the analyte. The method 900 may include associating positions and/or locations in the analyte with data such as visible light imaging data and Raman measurement data. The method 900 may include creating a composite data map of the analyte that includes a combination of visible light imaging data and Raman measurement data. The method 900 may include processing the visible light spectrum data and/or Raman spectrometer measurement data to form an overall view of the analyte.

In some configurations, the composite data map and/or the overall view of the analyte described above may be used to manually or automatically determine characteristics of a device, such as a sharpness of paring members of the device.

In some configurations, the method 900 may include transmitting electromagnetic radiation from an emitter to incident the first surface of the analyte. The method 900 may include moving a portion of an analyzation subassembly in one or more directions of movement with respect to the first surface of the analyte to scan at least a portion of the first surface of the analyte. The method 900 may include receiving electromagnetic radiation from the first surface of the analyte by the analyzation subassembly through the window. The method 900 may include identifying at least one characteristic of a component of the first surface of the analyte based on the electromagnetic radiation received from the first surface of the analyte.

In some configurations, the device 300 may include a detector such as a microphone, pressure sensor, strain gauge, force sensor, optical sensor or other suitable detector. The detector may be configured to gather information during at least a portion of the paring process. For example, the microphone may detect characteristics of the vibrations and/or sounds caused by the analyte 350 being pared by one or more of the paring members 332. The detected vibrations and/or sounds may be converted, for example, to electronic signals representing detector data. In other configurations, a pressure sensor, a force sensor, strain gauge, and/or an optical sensor may detect characteristics of the analyte 350 being pared by one or more of the paring members 332. The electronic signals and/or detector data may be used to identify characteristics of one or more of the: the analyte 350, one or more of the paring members 332, the paring process, and/or other characteristics of the system 40.

For example, the detector data may be used to identify when the mandrel subassembly 320 is forcing the analyte 350 against the paring subassembly 330 and/or the interface assembly 70 over a threshold force amount. In another example, the detector data may be used to identify when the mandrel subassembly 320 is forcing the analyte 350 against the paring subassembly 330 such that there is too much friction between the analyte 350 and the paring subassembly 330. Too much friction between the analyte 350 and the paring subassembly 330 may exist, for example, when the motor 360 is unable to move the mandrel subassembly 320 in the N direction because of the friction, and/or when there may be a risk of damaging the motor 360. In yet another example, the detector data may be used to identify when one or more of the paring members 332 becomes dull to a threshold value. The paring members 332 may be dull when their interaction with the analyte 350 creates vibrations and/or sounds with certain characteristics indicative of dullness. The detector may detect such vibrations and/or sounds and dullness may be identified via the detector data. In still another example, the detector data may be used to identify the structure and/or other characteristics of the analyte 350 based on the vibrations and/or sounds created when at least one of the paring members 332 interacts with the analyte 350.

In some configurations, the detector data may be processed by multi-variable analysis to detect any of the abovementioned characteristics and/or scenarios. In some configurations, the detector data may be processed to detect one or more specified changes in the characteristics of vibrations and/or sounds detected by the detector.

In some configurations, the detector and/or microphone may be used for analyzing the analyte 350. In such configurations, analyzing the analyte 350 may include obtaining the detector data. Analyzing the analyte 350 may include processing the detector data. Analyzing the analyte 350 may include combining the detector data with other data such as visible light imaging data and/or Raman measurement data. In some configurations, the detector data may be used in conjunction with other data such as visible light imaging data to analyze the analyte 350. The combined detector data and other data may be used to identify characteristics of one or more of the: the analyte 350, one or more of the paring members 332, the paring process, and/or other characteristics of the system 40.

In some configurations, the analyte 350 may be scanned to determine a dimension pared off of the analyte 350, such as a dimension of at least one of the layers 358a-n. In further configurations, the analyte 350 may be scanned to determine a volume of material pared off of the analyte 350. In such configurations, removed increments of the analyte 350 may be measured or estimated. The processing of the analyte 350 may be adapted based on information obtained from scanning the analyte 350. Based on the information obtained from scanning the analyte 350, variables such as analyte dimensions, analyte hardness, and/or the sharpness of the paring members may be obtained and/or estimated. Furthermore, such variables may be monitored over time as the processing of the analyte 350 continues. The processing of the analyte 350 may be dynamically controlled to achieve a specific amount of material removed for each of the layers 358a-n of the analyte 350. For example, the force of the paring members 332 on the analyte 350 may be adjusted based on the hardness of the analyte 350 and/or the sharpness of the parings members 332. In another example, as the paring members 332 become duller from use, the force of the paring members 332 on the analyte 350 may be dynamically increased to maintain a specific amount of material removed for each of the layers 358a-n of the analyte 350. In these and other configurations, a specified dimension of the layers 358a-n may be selected and other processing parameters may be varied to achieve the specified dimension.

In some configurations, the amount of force applied by the paring members 332 on the analyte 350 to remove a measured amount of material may be used to obtain and/or estimate the hardness of the analyte 350. Additionally or alternatively, the material removal rate may be obtained and/or estimated for the layers 358a-n to be used to obtain and/or estimate the hardness of the analyte 350.

Aspects of the present disclosure may be embodied in other forms without departing from its spirit or characteristics. The described aspects are to be considered in all respects illustrative and not restrictive. All changes which come within the meaning and range of equivalency of the claims are to be embraced within their scope.

What is claimed is:

1. A system for analyzing layers of an analyte, the system comprising:
a paring subassembly including at least one paring member sized and shaped to remove layers of an analyte to expose underlying surfaces of the analyte;
a mandrel subassembly including a mandrel defining a receptacle sized and shaped to retain the analyte as the layers of the analyte are removed;
an actuation subassembly to:
actuate the mandrel or the at least one paring member in one or more directions of movement with respect to one another to displace the analyte across the at least one paring member to remove a first layer of the analyte to expose a first surface; and
actuate the mandrel to position the exposed first surface of the analyte over a window of a hyperspectral analyzation subassembly to be scanned by the hyperspectral analyzation subassembly through the window.

2. The system of claim 1, the paring subassembly further including a housing defining a chamber to receive remnants of at least a portion of the removed first layer of the analyte.

3. The system of claim 2, the paring subassembly further including a fluid outlet in fluid communication with the chamber to evacuate the chamber.

4. The system of claim 1, wherein the at least one paring member includes at least one of:
a paring surface to remove at least a portion of the first layer by abrasion or frictional force; or
a paring edge to remove at least the portion of the first layer.

5. The system of claim 1, the paring subassembly further including a plurality of paring members arranged along an axis parallel to a first of the one or more directions of movement.

6. The system of claim 1, the actuation subassembly comprising:
a first actuator to actuate the mandrel subassembly in a first direction of movement of the one or more directions of movement; and
a first slide movably coupling the mandrel subassembly to the first actuator to accommodate movement of the mandrel subassembly in the first direction of movement by the first actuator.

7. The system of claim 6, the actuation subassembly further comprising:
a second actuator to actuate the mandrel subassembly in a second direction of the one or more directions of movement; and
a second slide movably coupling the mandrel subassembly to the second actuator and configured to accommodate movement of the mandrel subassembly in the second direction of movement by the second actuator.

8. The system of claim 7, the hyperspectral analyzation subassembly comprising:
one or more transmitters to generate electromagnetic radiation towards the analyte;
one or more sensors to detect electromagnetic radiation from the analyte; and
an analyzation actuation subassembly to actuate at least a portion of the hyperspectral analyzation subassembly to scan the analyte.

9. The system of claim 8, the hyperspectral analyzation subassembly further comprising:
an optical multiplexer to direct electromagnetic radiation travelling between the analyte and at least one of the one or more sensors and/or the one or more transmitters; and
an objective electromagnetically coupled between the window and the optical multiplexer to focus electromagnetic radiation travelling to or from the analyte.

10. The system of claim 8, the analyzation actuation subassembly further comprising:
a third actuator to actuate at least the portion of the hyperspectral analyzation subassembly in a third direction of movement of the one or more directions of movement;
a fourth actuator to actuate at least the portion of the hyperspectral analyzation subassembly in a fourth direction of movement of the one or more directions of movement; and
a fifth actuator to actuate at least the portion of the hyperspectral analyzation subassembly in a fifth direction of movement of the one or more directions of movement.

11. The system of claim 10, further comprising a computerized subassembly configured to one or more or a combination of:
transmit power and/or control signals to the actuation subassembly to actuate the mandrel;
transmit power and/or control signals to the analyzation actuation subassembly to scan the analyte; and
receive data from the hyperspectral analyzation subassembly to obtain information regarding the analyte.

12. The system of claim 11, wherein the information regarding the analyte includes information regarding a plurality of the layers of the analyte or a plurality of the exposed surfaces of the analyte, and the computerized subassembly is configured to generate a three-dimensional representation of the information regarding the analyte including physical structure and/or chemical makeup of the analyte.

13. The system of claim 1, the mandrel subassembly further comprising:
a mandrel holder to receive the mandrel; and
a mandrel clamp to retain the mandrel in the mandrel holder in a clamped position and to permit the mandrel to be inserted into the mandrel holder or removed from the mandrel holder in an unclamped position.

14. The system of claim 1, wherein the analyte is a pharmaceutical substance of a pill form.

15. A method of analyzing a plurality of layers of an analyte comprising:
for each of the plurality of layers:
shaving the layer of the plurality of layers to expose an underlying surface of the analyte;
after shaving, positioning the exposed surface of the analyte over a window of a hyperspectral analyzation subassembly; and
after positioning the exposed surface over the window, scanning the exposed surface of the analyte by the hyperspectral analyzation subassembly to obtain information regarding the analyte proximate the exposed surface; and
generating information regarding the plurality of layers of the analyte based at least in part on the obtained information.

16. The method of claim 15, wherein the shaving further comprises:
actuating a mandrel retaining the analyte in one or more directions to position the analyte against at least one paring member; and
displacing the analyte across the at least one paring member to remove the layer of the analyte to expose the underlying surface of the analyte.

17. The method of claim 15, wherein a paring subassembly includes a housing defining a chamber that receives remnants of at least a portion of the first layer removed from the analyte, the method further comprising evacuating the chamber of at least the a portion of the first layer removed from the analyte.

18. The method of claim 15, further comprising generating a three-dimensional representation of the analyte including physical structure and/or chemical makeup of the analyte, based on the obtained information.

19. The method of claim 15, further comprising:
transmitting electromagnetic radiation from an emitter to incident the exposed surface of the analyte;
moving a portion of an analyzation subassembly in one or more directions of movement with respect to the exposed surface of the analyte to scan at least a portion of the exposed surface of the analyte;
receiving electromagnetic radiation from the exposed surface of the analyte by the analyzation subassembly through the window; and
identifying at least one characteristic of a component of the analyte proximate the exposed surface based on the electromagnetic radiation received from the exposed surface of the analyte.

20. The method of claim 15, wherein the analyte is a chemical compound of a pill form or pharmaceutical substance of a pill form.

21. A filtered blade cartridge comprising:
a filtering device comprising:
a first housing defining a first chamber and an outlet conduit fluidly coupled to the first chamber;
a filter positioned inside of the first chamber and occluding the outlet conduit, wherein the filter permits fluids to pass through to the outlet conduit and separates solids to be collected in the first chamber; and
a paring subassembly comprising two or more paring members sized and shaped to remove layers of an analyte to expose underlying surfaces of the analyte.

22. The filtered blade cartridge of claim 21, further comprising
a second housing defining a second chamber and including one or more openings positioned in between the two or more paring members, the second chamber fluidly coupled to the first chamber.

23. The filtered blade cartridge of claim 21, wherein the first housing further defines a second chamber fluidly coupled to the first chamber and the outlet conduit, the filtering device further comprising a second filter positioned inside of the second chamber and occluding the outlet conduit, wherein the second filter permits fluids to pass through to the outlet conduit and separates solids to be collected in the second chamber.

* * * * *